United States Patent
Ito et al.

(10) Patent No.: US 6,423,725 B1
(45) Date of Patent: Jul. 23, 2002

(54) 4-(2-KETO-1-BENZIMIDAZOLINYL) PIPERIDINE COMPOUNDS AS ORL1-RECEPTOR AGONISTS

(75) Inventors: Fumitaka Ito, Chita-gun; Hirohide Noguchi, Seki; Yoriko Ohashi, Chita-gun; Hiroshi Kondo, Handa; Tatsuya Yamagishi, Chita-gun, all of (JP)

(73) Assignee: Pfizer INC, New York, NY (US)

(*) Notice: Subject to any disclaimer, the term of this patent is extended or adjusted under 35 U.S.C. 154(b) by 0 days.

(21) Appl. No.: 09/403,408
(22) PCT Filed: Jan. 8, 1999
(86) PCT No.: PCT/IB99/00012
§ 371 (c)(1), (2), (4) Date: Mar. 6, 2000
(87) PCT Pub. No.: WO99/36421
PCT Pub. Date: Jul. 22, 1999

(51) Int. Cl.[7] ............... A61K 31/454; C07D 211/06
(52) U.S. Cl. ............... 514/318; 514/322; 546/194; 546/199
(58) Field of Search ............... 514/318, 322; 546/194, 199

(56) References Cited

U.S. PATENT DOCUMENTS

| | | | |
|---|---|---|---|
| 3,161,645 A | 12/1964 | Janssen | 260/293.4 |
| 3,318,900 A | 5/1967 | Janssen | 260/294 |

FOREIGN PATENT DOCUMENTS

| | | | |
|---|---|---|---|
| EP | 0092391 | 10/1983 | A61K/31/445 |
| EP | 0322396 | 6/1989 | A61K/31/415 |
| WO | WO9716186 | 5/1997 | A61K/31/415 |
| WO | WO9723216 | 7/1997 | A61K/31/445 |
| WO | WO9740035 | 10/1997 | A61K/31/415 |
| WO | WO9854168 | 12/1998 | A61K/31/415 |

*Primary Examiner*—T. A. Solola
(74) *Attorney, Agent, or Firm*—Peter C. Richardson; Paul H. Ginsburg; Roy F. Waldron

(57) ABSTRACT

A compound of the formula:

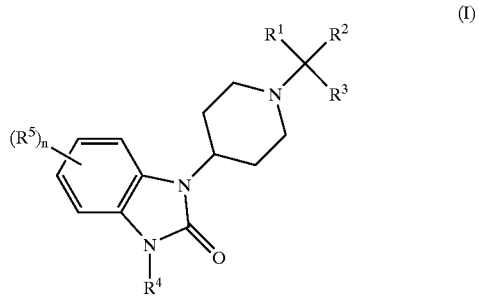

or the pharmaceutically acceptable salts thereof, wherein $R^1$, $R^2$, $R^3$, $R^4$ and $R^5$ are defined above are useful as ORL1-receptor agonists, and useful as analgesics or the like in mammalian subjects.

7 Claims, No Drawings

4-(2-KETO-1-BENZIMIDAZOLINYL) PIPERIDINE COMPOUNDS AS ORL1-RECEPTOR AGONISTS

This application is the U.S. National Stage under 35 U.S.C. §371 of PCT/IB99/00012, filed Jan. 8, 1999, which claims the benefit of earlier International application No. PCT/IB98/00069, filed Jan. 19, 1998.

TECHNICAL FIELD

This invention relates to novel 4-(2-keto-1-benzimidazolinyl)piperidine compounds or their pharmaceutically acceptable salts, pharmaceutical compositions containing them, and their medical uses. The compounds of this invention have activity as ORL1-receptor (opioid receptor-like 1 receptor) agonists, and as such are useful as an analgesic, anti-inflammatory, diuretic, anesthetic, neuroprotective, anti-hypertensive, or an anti-anxiety agent, or as an agent for appetite control or hearing regulation.

BACKGROUND ART

In spite of their usefulness as analgesics, usage of opioids such as morphine and heroin are strictly limited. This is because these drugs induce side effects such as euphoria or respiratory failure. Further, multiple dosage of the drugs cause addiction. Thus, there has been a long-felt need to provide less toxic analgesics.

Considerable pharmacological and biochemical studies have been carried out to identify opioid receptors and their endogenous ligands, and peptide and non-peptide opioid ligands have been discovered. In the recent past, amino acid sequences of $\mu$-, $\delta$- and $\kappa$-opioid receptor subtypes have been identified and reported. Subsequently, a novel receptor subtype was identified and termed ORL1-receptor, and Meunier, J.-C et al., reported the isolation and structure of the endogenous agonist of the receptor (*Nature*, Vol. 377, pp. 532–535, Oct. 12, 1995). It is suggested that the agonist for ORL1-receptor be effective in neurogenic inflammation (*Tips*, Vol. 18, pp. 293–300, August 1997). It is also suggested that the agonist be a potent analgesic having less psychological side effects and addiction (D. Julius, *Nature*, Vol. 377, p. 476, Oct. 12, 1995).

WO 97/40035 and U.S. Pat. No. 3,318,900 disclose a series of benzimidazolinyl piperidines.

BRIEF DISCLOSURE OF THE INVENTION

The present invention provides a compound of the following formula:

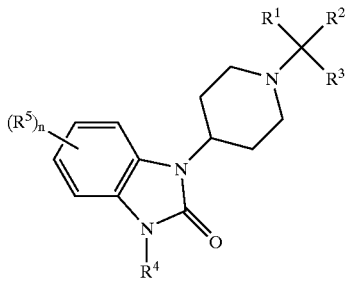

(I)

or the pharmaceutically acceptable salts thereof, wherein $R^1$ and $R^2$ are independently $C_1$–$C_4$ alkyl; or $R^1$ and $R^2$, taken together with the carbon atom to which they are attached, form a mono-, bi-, tri- or spiro-cyclig group having 6 to 13 carbon atoms, wherein the cyclic group is optionally substituted by one to five substituents independently selected from $C_1$–$C_4$ alkyl, $C_2$–$C_4$ alkylene, $C_1$–$C_4$ alkoxy, hydroxy, oxo, $=CH_2$ and $=CH$—$C_1$–$C_4$ and alkyl;

$R^3$ is $C_1$–$C_7$ alkyl, $C_2$–$C_5$ alkenyl, $C_2$–$C_5$ alkynyl, phenyl-$C_1$–$C_5$ alkyl, phenyl optionally substituted by one to three substituents independently selected from fluorine, $C_1$–$C_3$ alkyl and $C_1$–$C_3$ alkoxy, or a heteroaryl group selected from furyl, thienyl, pyrrolyl and pyridyl, wherein said heteroaryl group is optionally substituted by one to three substituents independently selected from halo, $C_1$–$C_3$ alkyl and $C_1$–$C_3$ alkoxy, with the proviso that when both $R^1$ and $R^2$ are $C_1$–$C_4$ alkyl, then $R^3$ is other than $C_1$–$C_7$ alkyl, $C_2$–$C_5$ alkenyl and $C_2$–$C_5$ alkynyl;

$R^4$ is selected from:
1) hydrogen,
2) optionally mono- or di-substituted, $C_1$–$C_8$ alkyl, $C_3$–$C_7$ cycloalkyl, $C_2$–$C_8$ alkenyl, $C_2$–$C_8$ alkynyl, $C_1$–$C_6$ alkyl-Z—, $C_1$–$C_6$ alkyl-Z—$(C_1$–$C_6)$alkyl, $C_3$–$C_7$ cycloalkyl-Z—$(C_1$–$C_6)$alkyl, $C_2$–$C_6$ alkenyl-Z—$(C_1$–$C_6)$alkyl or $C_2$–$C_6$ alkynyl-Z—$(C_1$–$C_6)$ alkyl, wherein Z is selected from O, S, SO, $SO_2$, CO, $CO_2$, OCO, NR, CONR and NRCO, wherein R is hydrogen or $C_1$–$C_6$ alkyl, and the substituents to be attached to the alkyl, alkenyl, alkynyl or cycloalkyl moiety are independently selected from halo, hydroxy, carboxy, amino, mono- or di-($C_1$–$C_4$ alkyl) amino, hydrazino, azido, ureido, amidino and guanidino; or
3) optionally mono- or di-substituted, aryl, heterocyclic, aryl($C_1$–$C_5$)alkyl, heterocyclic($C_1$–$C_5$) alkyl, heterocyclic-heterocyclic($C_1$–$C_5$)alkyl, aryl-heterocyclic($C_1$–$C_5$)alkyl, heterocyclic-Z—$(C_1$–$C_5$) alkyl, aryl-Z—$(C_1$–$C_5$)alkyl, aryl($C_1$–$C_5$ )alkyl-Z— $(C_1C_5$ )alkyl, or heterocyclic($C_1$–$C_5$ )alkyl-Z— $(C_1$–$C_5$)alkyl, wherein Z is selected from O, S, SO, $SO_2$, CO, $CO_2$, OCO, NR, CONR and NRCO, wherein R is hydrogen or $C_1$–$C_6$ alkyl, and the substituents to be attached to the aryl or heterocyclic moiety are independently selected from halo, hydroxy, carboxy, $C_1$–$C_4$ alkyl, halo $C_1$–$C_4$alkyl, $C_1$–$C_4$ alkoxy, $C_1$–$C_4$ alkyl-CO—, amino($C_1$–$C_4$) alkyl-CO—, phenyl, benzyl, amino, mono- or di-($C_1$–$C_4$ alkyl)amino, hydrazino, azido, ureido, amidino and guanidino;

$R^5$ is independently selected from halo, $C_1$–$C_3$ alkyl, $C_1$–$C_3$ alkoxy, $C_1$–$C_3$ alkylsulfonyl, $CF_3$, carboxy, hydroxy, amino, alkylamino, acylamino, arylcarbonyl, alkylcarbonyl and hydroxyalkyl; and n is 0, 1, 2, 3 or 4.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "halo", as used herein, refers to F, Cl, Br or I, preferably F or Cl.

The term "$C_2$–$C_4$ alkylene" means a straight or branched radical formed from an unsaturated aliphatic hydrocarbon such as ethenyl, propenyl or butenyl.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "aryl", as used herein, means a monocyclic or bicyclic aromatic carbocyclic ring system of 6–11 carbon atoms including, but not limited to, phenyl, naphthyl, indanyl, (1,2,3,4)-tetrahydronaphthyl, indenyl, isoindenyl and the like.

The term "heterocyclic" means a monocyclic or bicyclic hydrocarbon ring system which has one or more hetero atoms in the ring, preferably has 4 to 10 carbon atoms and 1 to 3 heteroatoms including, but not limited to, piperidino, hexamethyleneimino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl, quinolyl, thiophenyl, pyrazinyl, pyridazinyl, aziridinyl and azetidinyl.

The term "bi- or tri-cyclic ring" means hydrocarbon cyclic groups of 6 to 16 carbon atoms, having two to three rings therein, including, but not limited to, decahydronaphthalene, bicyclo[2.2.1.]heptane, bicyclo[3.2.1]octane, bicyclo[3.3.1]nonane, adamantane and tricyclo[5.2.1.0$^{2,6}$]decane.

The term "spirocyclic group" means a hydrocarbon spirocyclic group of 6 to 13 carbon atoms, including, but not limited to, spiro[5.5]undecanyl and spiro[4.5]decanyl.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred group of the compounds of the present invention includes the compound of Formula (I), wherein $R^1$ and $R^2$ are independently $C_1$–$C_4$ alkyl; or $R^1$ and $R^2$, taken together with the carbon atom to which they are attached, form a monocyclic group selected from cyclo-$C_3$–$C_{14}$ alkyl and cyclo-$C_4$–$C_{14}$ alkenyl, a bicyclic group selected from decahydronaphthalene, bicyclo[2.2.1.]heptane, bicyclo[4.3.0]nonane, bicyclo[3.2.1]octane, bicyclo[3.2.0]heptene and bicyclo[3.3.1]nonane, a tricyclic group selected from adamantane and tricyclo[5.2.1.0$^{2,6}$]decane, or a spirocyclic group selected from spiro[5.5]undecanyl and spiro[4.5]decanyl, wherein the cyclic group is optionally substituted by one to three substituents independently selected from $C_1$–$C_4$ alkyl, $C_2$–$C_4$ alkylene, $C_1$–$C_4$ alkoxy, hydroxy and oxo;

$R^3$ is $C_1$–$C_7$ alkyl, $C_2$–$C_5$ alkenyl, $C_2$–$C_5$ alkynyl, phenyl-$C_1$–$C_5$ alkyl, phenyl optionally substituted by one to three substituents independently selected from fluorine, $C_1$–$C_3$ alkyl and $C_1$–$C_3$ alkoxy, or thienyl;

$R^4$ is selected from:

1) hydrogen;

2) optionally mono- or di-substituted, $C_1$–$C_8$ alkyl, $C_3$–$C_7$ cycloalkyl, $C_2$–$C_6$ alkenyl, $C_1$–$C_6$ alkyl-Z—($C_1$–$C_6$)alkyl, $C_3$–$C_7$ cycloalkyl-Z—($C_1$–$C_6$)alkyl or $C_2$–$C_6$ alkenyl-Z—($C_1$–$C_6$)alkyl, wherein Z is selected from NH, O, S, SO, $SO_2$, CO, $CO_2$, OCO, CONH and NHCO, and the substituents are independently selected from halo, hydroxy, amino, mono- or di-($C_1$–$C_4$ alkyl)amino, hydrazino, azido, ureido, amidino and guanidino; or 3) optionally mono- or di-substituted, aryl, heterocyclic, aryl($C_1$–$C_5$)alkyl, heterocyclic($C_1$–$C_5$) alkyl, heterocyclic-piperazino($C_1$–$C_5$)alkyl, heterocyclic-amino($C_1$–$C_5$)alkyl, heterocyclic-Z—($C_1$–$C_5$)alkyl, aryl-Z—($C_4$–$C_5$)alkyl, aryl($C_1$–$C_5$) alkyl-Z—($C_1$–$C_5$)alkyl or heterocyclic($C_1$–$C_5$)alkyl-Z—($C_1$–$C_5$)alkyl, wherein the aryl group is selected from phenyl and naphthyl, and the heterocyclic group is selected from furyl, thiophenyl, pyridyl, pyrimidiny, pyrazinyl, pyridazinyl, aziridinyl, azethidinyl, pyrrolidinyl, piperidino, hexamethyleneimino, piperazino and morpholino;

Z is selected from NH, O, S, SO, $SO_2$,CO, $CO_2$, OCO, CONH and NHCO; and the substituents are independently selected from halo, hydroxy, carboxy, $C_1$–$C_4$ alkyl, halo $C_1$–$C_4$ alkyl, $C_1$–$C_4$ alkoxy, $C_1$–$C_4$ alkyl-CO—, phenyl, benzyl, amino, mono- or di-($C_1$–$C_4$ alkyl)amino, hydrazino, azido, ureido, amidino and guanidino; and $R^5$ is halo, $CF_3$ or $C_1$–$C_3$ alkoxy; and n is 0, 1, 2or 3.

A more preferred group of this invention includes the compounds of Formula (I), wherein $R^1$ and $R^2$, taken together with the carbon atom to which they are attached, form a cyclic group selected from cyclopropyl, cyclobutyl, cyclopentyl, cyclohexyl, cycloheptyl, cyclooctyl, cyclononyl, cyclodecyl, cycloundecyl, cycloheptenyl, dimethylcyclohexyl, butylcyclohexyl, isopropylidenecyclohexyl, bicyclo[4.3.0]nonanyl and spiro[5.5]undecanyl; $R^3$ is $C_1$–$C_3$ alkyl, $C_7$–$C_3$ alkenyl, phenyl optionally substituted by chloro, fluoro or $C_1$–$C_3$ alkoxy, phenyl($C_1$–$C_3$)alkyl, ethenyl or thienyl; $R^4$ is hydrogen, ($C_1$–$C_6$)alkyl, ($C_1$–$C_6$)alkyl substituted by amino, guanidino, ($C_1$–$C_3$)alkylamino, acetylamino, pyrroryl-CO—NH—, pyridyl-CO—NH—, heterocyclic selected from piperidino, hexamethyleneimino, morpholino, pyrrolidino, pyrrolyl, pyridinyl, pyrimidinyl and pyrimidinylpiperazino; R5 is fluoro, chloro, ($C_1$–$C_3$)alkyl or ($C_1$–$C_3$) alkoxy; and n is 0, 1 or 2.

Preferred individual compounds of this invention are following:

1-{1-[1-Methyl-1-(2-thienyl)ethyl]-4-piperidinyl}-1,3-dihydro-2H-1,3-benzimidazol-2-one, 1-[1-(1-Phenylcycloheptyl)-4-piperidinyl]-1,3-dihydro-2H-1,3-benzimidazol-2-one, 1-[4-Piperidinyl-1-(1-Propylcyclononyl)]-1,3-dihydro-2H-1,3-benzimidazol-2-one, 1-[1-(1-Phenylcyclooctyl)-4-piperidinyl]-1,3-dihydro-2H-1,3-benzimidazol-2-one, 1-[1-(1-Phenylcyclononyl)-4-piperidinyl]-1,3-dihydro-2H-1,3-benzimidazol-2-one, 1-{1-[1-(4-Fluorophenyl)cycloheptyl]-4-piperidinyl}-1,3-dihydro-2H-1,3-benzimidazol-2-one, 1-[1-(1-Methylcyclononyl)-4-piperidinyl]-1,3-dihydro-2H-1,3-benzimidazol-2-one, 1-[1-(1-Ethylcyclononyl)-4-piperidinyl]-1,3-dihydro-2H-1,3-benzimidazol-2-one, 1-[1-(1-Methylcyclooctyl)-4-piperidinyl]-1,3-dihydro-2H-1,3-benzimidazol-2-one, 1-[1-(1-Phenylcyclohept-4-enyl)-4-Piperidinyl]-1,3-dihydro-2H-benzimidazol-2-one, 1-(2-Aminoethyl)-3-[1-(1-phenylcycloheptyl)-4-piperidinyl]-1,3-dihydro-2H-benzimidazol-2-one, 1-(6-Aminohexyl)-3-[1-(1-phenylcycloheptyl)-4-piperidinyl]-1,3-dihydro-2H-benzimidazol-2-one, 1-(2-Aminoethyl)-3-[1-(1-phenylcyclohept-4-enyl)-4-piperidinyl]-1,3-dihydro-2H-benzimidazol-2-one, 1-[1-(1-phenylcycloheptyl)-4-piperidinyl]-3-(2-piperidinoethyl)-1,3-dihydro-2H-benzimidazol-2-one, and a salt thereof.

The most preferred compounds are:

1-[1-(phenylcycloheptyl)-4-piperidinyl]-1,3-dihydro-2H-1,3-benzimidazol-2-one, 1-[1-(1-methylcyclononyl)-4-piperidinyl]-1,3-dihydro-2H-1,3-benzimidazol-2-one, 1-[1-(1-methylcyclooctyl)-4-piperidinyl]-1,3-dihydro-2H-1,3-benzimidazol-2-one, 1-(6-aminohexyl)-3-[1-(1- phenylcycloheptyl)-4-piperidinyl]-1,3-dihydro-2H-benzimidazol-2-one, 1-[1-(1-phenylcycloheptyl)4-piperidinyl]-3-(2-piperidinoethyl)-1,3-dihydro-2H-benzimidazol-2-one, and a salt thereof.

The present invention also relates to a pharmaceutical composition for the treatment of a disorder or condition mediated by ORL1-receptor and its endogenous ligands in a mammal, including a human, which comprises an effective amount of the compound of Formula (I), or a pharmaceutically acceptable salt thereof and a pharmaceutically acceptable carrier.

The present invention also relates to a method for treating a disorder or condition, the treatment of which can be effected or facilitated by binding to ORL1-receptor in a mammal, including a human, comprising administering to a mammal in need of such treatment an effective amount of a compound of Formula (I), or a pharmaceutically acceptable salt thereof.

The compounds of Formula (I) of this invention can be useful as an analgesic, anti-inflammatory, diuretic, anesthetic, neuroprotective, anti-hypertensive or an anti-anxiety agent, or an agent for appetite control or hearing regulation. The compounds of Formula (I) of this invention can be used as agents for the treatment of the other psychiatric, neurological and physiological disorders such as depression, trauma, memory loss due to Alzheimer's disease or other dementias, epilepsy and convulsions, symptoms of withdrawal from drugs of addiction, control of water balance, sodium excretion, and arterial blood pressure disorders.

DETAILED DISCLOSURE OF THE INVENTION

The following reaction Schemes illustrate the preparation of the compounds of the present invention. Unless otherwise indicated, $R^1$, $R^2$, $R^3$, $R^4$, $R^5$ and $R^6$ in the reaction Schemes and discussion that follow are defined above.

General Synthesis

The ORL1 agonists of Formula (I) of this invention may be prepared according to the following methods.

Reaction Scheme 1 illustrates a method for the preparation of Compound (I).

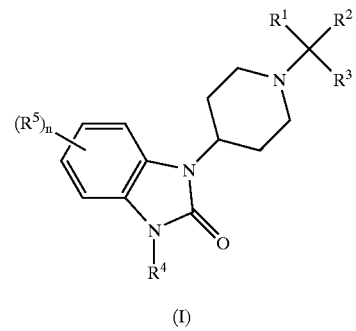

(I)

As shown in Scheme 1, Compounds (I) may be obtained from benzimidazolinylpiperidine compound (II) via intermediate (IV). First, Compound (II) may be subjected to the Strecker synthesis with the stoichiometric amount of ketone (III). Second, Compound (IV) can be subjected to Grignard reaction with a reagent represented by the formula $R^3MgX$ (X is such as halo) to give Compound (I).

The Strecker synthesis can be carried out using a suitable cyanating agent according to known procedures reported by A. Kalir, et al., (*J. Med. Chem.* 1969, 12, 473). Suitable cyanating agents include cyanide such as potassium cyanide (KCN). This reaction can be carried out at pH of about 3 to 11 in ice-cool water for 30 min to 7 days. The Grignard reaction can be carried out under unhydrous condition according to known procedures (e.g., O. A. Al-Deeb. *Arzneim.-Forsch./Drug Res.*, 1994, 44, 1141). More specifically, this reaction can be carried out in a suitable solvent such as tetrahydrofuran (THF), at from about room temperature to the reflux temperature of the solvent for 30 minutes to 48 hours.

Compounds of the Formula (I) can be also prepared by the methods illustrated in Scheme 2.

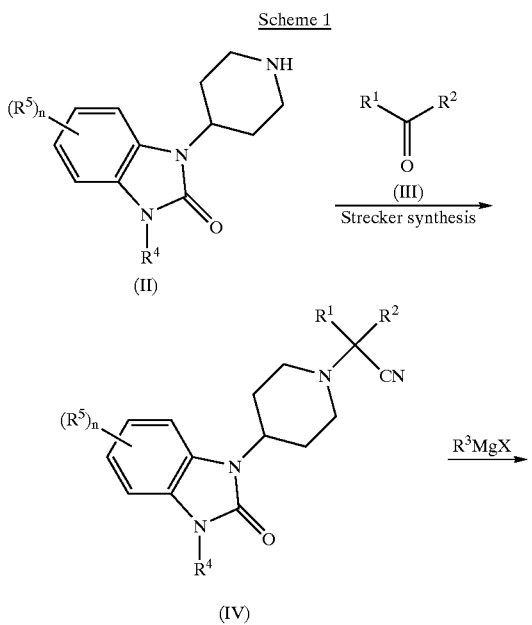

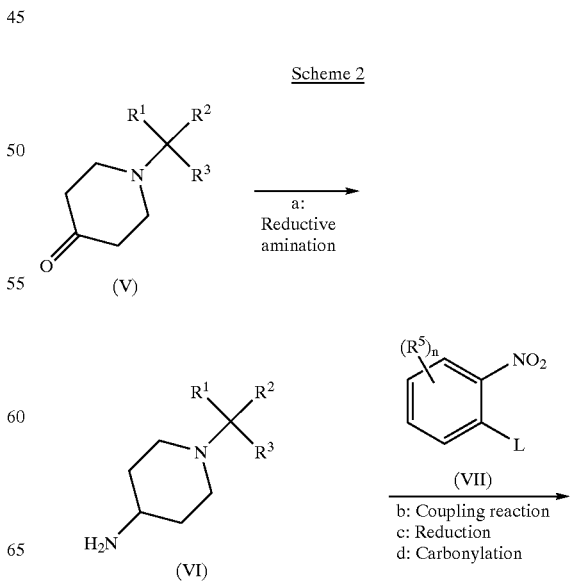

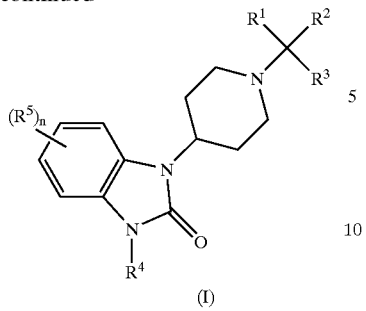

As shown in Scheme 2, Compounds (I) wherein $R^4$ is hydrogen can be prepared through the steps comprising (a) reductive amination of a piperidine4-one (V) to give the 4-aminopiperidine (VI), (b) coupling reaction of the compound (VI) with a nitrobenzene (VII), (c) reduction of the resultant product of step (b), and (d) carbonylation reaction of the resultant product of step (c). Each reaction step is described below.

(a) The reductive amination of Compound (V) can be carried out under known conditions. For example, this reductive amination can be carried out in the presence of a reducing agent such as sodium cyanoborohydride (NaBH$_3$CN) and ammonium acetate, in a suitable solvent such as methanol at about room temperature for about 1 hour to 2 days (U.S. Pat. No. 5,124,457). The reductive amination can also be carried out according to the procedures reported by B. de Costa et al., *J. Chem. Soc., Perkin Trans.* 1, 1992, 1671.

(b–d) Steps (b) through (d) can be achieved by known procedures reported for example by N. A. Meanwell et al., *Bioorganic & Medicinal Chemistry Letters*, 1996, 6, 1641. More specifically, the coupling reaction (b) can be carried out in the presence of potassium carbonate (K$_2$CO$_3$) in acetonitrile with heating. The reduction (c) can be carried out in the presence of a reducing agent such as tin (II) chloride in a polar solvent such as ethanol with heating. The carbonylation (d) can be carried out in the presence of a carbonylating agent such as carbonyldiimidazole or trichloromethyl chloroformate in a reaction inert solvent such as tetrahydrofuran (THF) with heating.

Compounds (I) wherein $R^4$ is $C_1$–$C_4$ alkyl can be obtained by alkylation of Compound (I) wherein $R^4$ is hydrogen using a desired alkylating agent. This alkylation can be carried out in the presence of a reaction inert solvent such as DMF, in the presence of strong base such as sodium hydride, at a temperature from about 0° C. to room temperature, for 1 minute to 6 hours. Suitable alkylating agents are such as alkylhalides or mesylate.

Compounds (I) wherein $R^1$ and $R^2$, taken together with the carbon atom to which they are attached, form a monocyclic, bicyclic or spirocyclic ring can be prepared by subjecting an intermediate (II) to the Grignard reaction according to the similar procedures illustrated in Scheme 1. The suitable Grignard reagents are those represented by the formula of $R^1R^2R^3CMgX$ wherein $R^1$ and $R^2$, taken together with the carbon atom to which they are attached, form a monocyclic or bicyclic ring; and X is halo.

Intermediates (V) can be prepared by the methods illustrated in Scheme 3.

Scheme 3

Route 1:

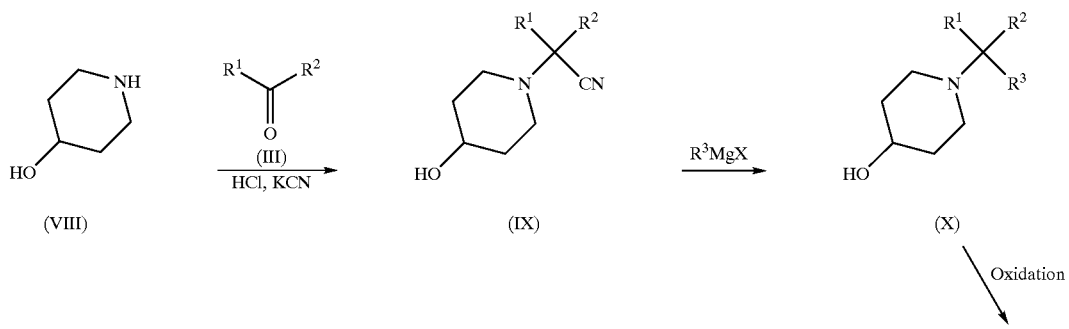

Route 2:

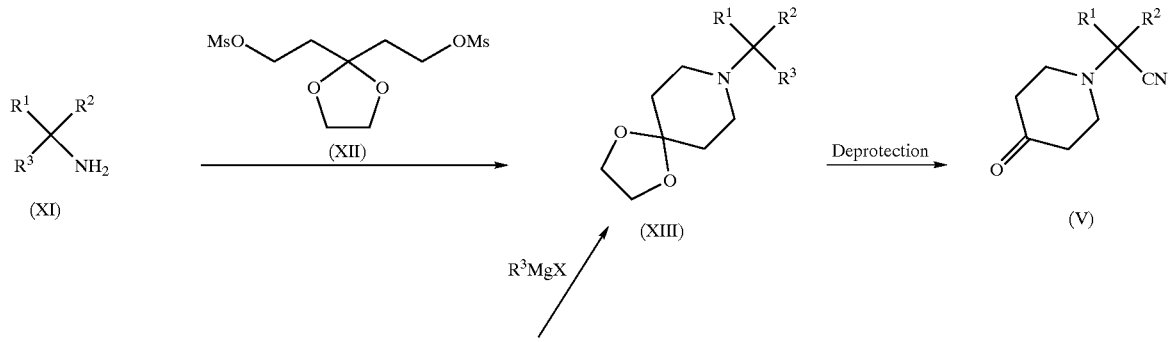

Route 3:

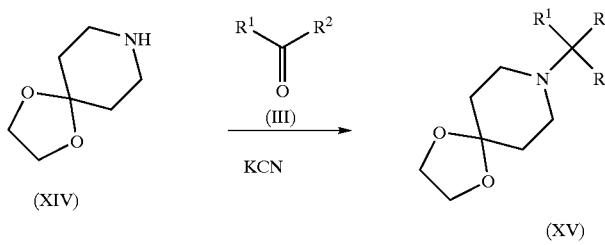

Route 1 illustrates a preparation of Compound (V) from known 4-piperidinol (VIII) according to the procedures reported by A. Kalir et al., *J. Med. Chem.*, 1969, 12, 473. First, Compound (VIII) can be condensed with Compound (III) and cyanated to give Compound (IX). Second, obtained Compound (IX) can be subjected to the Grignard reaction with $R^3MgX$ wherein X is halo to give Compound (X). Then, Compound (X) can be oxidized to give Compound (V).

Route 2 illustrates a preparation of Compound (V) from a starting amine (XI) comprising condensation of (XI) with 3,3-ethylenedioxypentane-1,5-diol dimethanesulfonate (XII) followed by deprotection. These reactions can be carried out under known conditions (e.g., B. de Costa et al., *J. Chem. Soc., Perkin Trans.* I. 1992, 1671). Compound (V) can be prepared directly from a starting amine (XI) using N-ethyl-N-methyl4-oxopiperidinium iodide according to the procedure of D. M. Tschaen et al (*J. Org. Chem.* 1995, 60, 4324).

Route 3 illustrates a preparation of Compound (V) from a known oxygen protected piperidine-4-one (XIV). This preparation comprises (a) condensation of (XIV) with (III), (b) cyanation, (c) the Grignard reaction and (d) deprotection. These reactions can be carried out under the same conditions described in Scheme 1.

The starting amines (XI) can be readily prepared by known methods for a skilled person (e.g., J. Weinstock, et al., OS IV 910, E. J. Cone, et al., *J. Med. Chem.*, 1981, 24, 1429, and Ritter Reaction described in Org. React., 1969, 17, 313).

Compound (II) can be prepared by known methods as illustrated in Scheme 4.

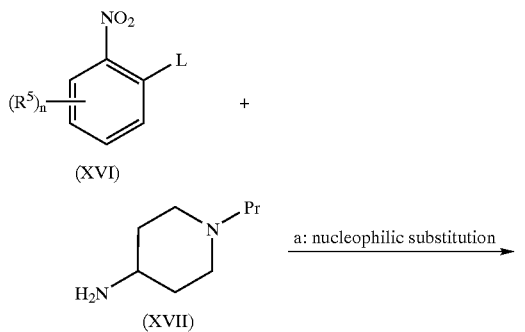

In Scheme 4, Compound (II) can be prepared by the method comprising (a) nucleophilic substitution of (XVI) with (XVII), (b) reduction of (XVIII), (c) carbonylation, (d) alkylation of (XIX) and (e) deprotection of (II').

(a) Nucleophilic substitution of (XVI) with (XVII):
A substituted nitrobenzene (XVI) wherein L is a leaving group, can be subjected to nucleophilic substitution with an aminopiperidine (XVII) wherein Pr is a protecting group, to give the compound (XVIII). Suitable leaving groups include halo, preferably F. Suitable N-protecting groups include benzyl, benzyloxycarbonyl and tert-butyloxycarbonyl, preferably benzyl. This reaction can be carried out in the presence of a metal catalyst such as copper (II) oxide, and weak base such as potassium carbonate, at from about 100° C. to 300° C. for about 30 minutes to 48 hours (preferably at 150° C. to 250° C. for 60 minutes to 24 hours).

(b, c) Reduction and Carbonylation of (XVIII):
Compound (XVIII) can be reduced and carbonylated to give the amine (XIX). The reduction can be carried out in the presence of a reducing agent in a polar solvent. Suitable reducing agents include metal halide such as tin (II) chloride hydrate ($SnCl_2$—$H_2O$), and suitable polar solvents include alcohol such as ethanol. This reaction can be carried out at up to the reflux temperature of the reaction mixture for 30 minutes to 24 hours. The subsequent carbonylation can be carried out according to the known procedures. These procedures are reported for example by N. A. Meanwell et al., *Bioorganic & Medicinal Chemistry Letters,* 1996, 6, 1641 (also referred to in Scheme 2) and R. Iemura et al., *Chem. Pharm. Bull.,* 1989, 37, 962.

(d) Alkylation of (XIX):

Compound (XIX) can be alkylated to give Compound (II') by known methods. For example, this alkylation can be carried out by reacting Compound (XIX) with a suitable alkylating agent such as alkyl halide. This reaction can be carried out in the presence of a base such as sodium hydride (NaH) in a reaction inert solvent such as dimethylformamide at about room temperature for 30 minutes to 24 hours.

(e) Deprotection of (II'):

The protecting group of Compound (II') can be removed by conventional method, for example, by catalytic hydrogenation to give Compound (II). This catalytic hydrogenation can be conducted in a polar solvent such as alcohol (e.g., methanol and ethanol), under hydrogen at about room temperature, for from about 30 minutes to 48 hours. Suitable catalysts are noble metal catalysts such as palladium (II) hydroxide on carbon.

The starting materials (XVI) and (XVII) are known compounds, and can be prepared according to known procedures for a person skilled in the art.

To the 3-position of the benzimidazole ring, several functional groups ($R^4$) can be introduced by methods known to those skilled in the art. For example, the compounds of formula (I) wherein $R_4$ is H, can be reacted with $R_4$—L (L is a leaving group such as halo or MsO) in the presence of a base such as sodium hydride(NaH) in a reaction inert solvent such as tetrahydrofuran (THF) and dimethylformamide (DMF) at about 0° C. to 80° C. for 20 minutes to 24 hours. When $R_4$—L has a terminal amino group, it can be protected by an amino-protecting group such as tert-butoxycarbonyl during the above reaction. The amino-protecting group can be removed from the resultant product by a conventional method, for example, by treatment with hydrochloric acid in methanol. If required, the resultant terminal amino group can be further reacted with X-halo (X is heteroaryl, etc.) to attach the X group thereto. The terminal amino group can be also reacted with an acylating agent such as X—CO—Cl, X—COOH, or its acid anhydride.

Unless indicated otherwise, the present pressure of each of the above reactions is not critical. Generally, the reactions will be conducted at a pressure of about one to about three atmosphere, preferably at ambient pressure (about one atmosphere).

The compounds of Formula (I) of this invention are basic, therefore they will form acid-addition salts. All such salts are within the scope of this invention. However, it is necessary to use an acid addition salts which is pharmaceutically-acceptable for administration to a mammal. The acid-addition salts can be prepared by standard methods. For example, the salts may be prepared by contacting the basic compounds with acid in substantially equivalent proportions in water or an organic solvent such as methanol or ethanol, or a mixture thereof. The salts can be isolated by crystallization from or evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, p-toluenesulfonate, oxalate and pamoate (1,1'-methylene-bis-(2-hydroxy-3-naphtoate)) salts.

The compounds of Formula (I) have been found to possess selective affinity for ORL1-receptors and ORL-1 receptor agonist activity. Thus, these compounds are useful as an analgesic, anti-inflammatory diuretic, anesthetic, neuroprotective, anti-hypertensive or an anti-anxiety agent, or an agent for appetite control or hearing regulation, in mammalian subjects, especially humans in need of such agents. These compounds are also useful as agents for the treatment of the other psychiatric, neurological and physiological disorders such as depression, trauma, memory loss due to Alzheimer's disease or other dementias, epilepsy and convulsions, symptoms of withdrawal from drugs of addiction, control of water balance, sodium excretion, and arterial blood pressure disorders.

The affinity, agonist activities and analgesic activity can be demonstrated by the following tests respectively. Within the following descriptions of these tests, "SPA" means ($\alpha$,R)-N,N-dimethyl-$\alpha$-phenyl-benzeneethanamine hydrochloride; "CHO-K1" refers to Chinese Hamster Ovary cells (ATCC No. CCL-61); "CI-977" refers to, N-methyl-N-[(5R, 7S,8S)-7-(1-pyrrolidinyl)-1-oxiaspiro[4.5]dec-8-yl]-4-benzofuranacetamide monohydrochloride; "DPDPE" refers to [2-D-Penicillamine, 5-D-Pencilliamine]enkephalin; "DAMGO" refers to L-tyrosyl-D-alanylglycyl-N-(2-hydroxyethyl)-N$\alpha$-methyl-L-phenylalaninamide; "HEK" refers to (N-2-hydroxyethylpiperazine-N'-2-ethane sulfonic acid); and "ICR" refers to a strain of mouse designated Tac:Icr:Ha(ICR) (Taconic Farms Inc., Germantown, N.Y.).

Selective Affinity for ORL1-receptors

ORL1-receptor Affinity

The ORL1 receptor binding affinity of the compounds of this invention are determined by the following procedures. Human ORL1 receptor transfected HEK-293 cell membranes and wheat-germ agglutinin coated SPA beads are combined with 0.4 nM[3H]nociceptin and unlabeled test compounds in 200 μl of 50 mM Hepes buffer pH7.4 containing 10 mM $MgCl_2$ and 1 μM EDTA. This mixture is incubated at room temperature (abbreviated as rt) for 30 min to 60 min. Non specific binding is determined by the addition of 1 μM nociceptin. Radioactivity is counted by Wallac 1450 MicroBeta.

μ-receptor Affinity

The mu (μ) opioid receptor binding affinity of the compounds of this invention are determined by the following procedures. Human-mu opioid receptor transfected CHO-K1 cell membranes and wheat-germ agglutinin coated SPA beads are combined with 1.0 nM[3H]DAMGO and unlabeled test compounds in 200 μl of 50 mM Hepes buffer pH7.4 containing 10 mM $MgCl_2$ and 1 mM EDTA. This mixture is incubated at rt for 30 min to 60 min. Non specific binding is determined by the addition of 1 μM DAMGO. Radioactivity was counted by Wallac 1450 MicroBeta.

κ-receptor Affinity

The kappa (κ) opioid receptor binding affinity of the compounds of this invention are determined by the following procedures. Human kappa-opioid receptor transfected CHO-K1 cell membranes and wheat-germ agglutinin coated SPA beads are combined with 0.5 nM[3H]CI-977 and unlabeled test compounds in 200 μl of 50 mM Hepes buffer pH7.4 containing 10 mM $MgCl_2$ and 1 mM EDTA. This mixture is incubated at rt for 30 min to 60 min. Non specific binding is determined by the addition of 1 μM CI-977. Radio activity is counted by Wallac 1450 MicroBeta.

δ-receptor Affinity

The delta (δ) opioid receptor binding affinity of the compounds of this invention are determined by the following procedures. Human delta opioid receptor transfected CHO-K1 cell membranes and wheat-germ agglutinin coated SPA beads are combined with 2.0 nM[3H]DPDPE and unlabeled test compounds in 200 μl of 50 mM Hepes buffer pH7.4 containing 10 mM $MgCl_2$ and 1 mM EDTA. The assay is incubated at room temperature for 30 min to 60 min. Non specific binding are determined by the addition of 1 μM of each non-labeled ligands. Radioactivity is counted by Wallac 1450 MicroBeta.

Each percent non specific binding thus obtained is graphed as a function of compound concentration. A sigmoidal curve is used to determine $IC_{50}$ values.

All compounds of Example 1 through 89 were tested by the above procedures and demonstrated good affinity for ORL1-receptors, or lower affinity for mu-receptors. In this testing, the above-mentioned preferred compounds demonstrated higher affinity for ORL1-receptors than for mu-receptors (i.e., $IC_{50}$ for ORL1-receptors/$IC_{50}$ for mu-receptors were less than 1.0).

Functional Assay

The functional activity of the compounds of this invention in each opioid receptor can be determined in 35S-GTPγS binding system according to the procedures reported by L. J. Sim, R. Xiao and S. Childers *Neuroreort* Vol. 7, pp. 729–733, 1996. Each human ORL1-, mu-, kappa- and delta-receptor transfected CHO-K1 or HEK cell membranes are used. The membranes are suspended in ice-cold 20 mM HEPES buffer pH 7.4, containing 100 mM NaCl, 10 mM $MgCl_2$ and 1 mM EDTA. 0.17 mg/ml of Dithiothreitol (DTT) is added to this buffer prior to use. Membranes are incubated at 25° C. for 30 minutes with the appropriate concentration of test compounds in the presence of 5 μM GDP, 0.4 nM of 35S-GTPγS and Wheat-germ agglutinin (WGA) coated SPA bead (1.5 mg) in a 0.2 ml total volume. Basal binding is assessed in the absence of agonist, and non-specific binding is determined with 10 μM GTPγS. Radio activity is counted by Wallac 1450 MicroBeta.

Analgesic Tests

Tail Flick Test

Male ICR mice, 4 weeks old and weighing 19–25 g, are used. The training sessions are performed until mice can flick their tails within 4.0 sec by using Analgesia Meter MK-330A (Muromachi Kikai, Japan). Selected mice are used in this experiment. The latency time is recorded twice at 0.5, 1.0, and 2.0 h after administration of the compound. The intensity of the beam is set to 80. Cut-off time is set to 8.0 sec. A compound of this invention is subcutaneously administered 30 min before the test. The $ED_{50}$ value, defined as the dose of the compounds tested which halves the tail flicking is observed in the control group.

Acetic Acid Writhing Test

Male ICR mice, 4 weeks old and weighing 21–26 g, are used. They are fasted the day before use. Acetic acid is diluted with saline to the concentration of 0.7%(v/v) and injected intraperitoneally (0.2 ml/10 g of body weight) to mice with a 26 gauge needle. A compound of this invention is dissolved in 0.1% methyl cellulose(MC)-saline and subcutaneously administered to mice 0.5 h before acetic acid injection. After the acetic acid injection, each animal is placed in a IL beaker and recorded by a video tape recorder. Number of writhing is counted from 5 to 15 min after acetic acid injection. The $ED_{50}$ value, defined as the dose of the compounds tested which halves the writhing is observed in the control group. Some compounds of this invention demonstrated good analgesic activity in this test (i.e., $ED_{50}$ value of 0.02 mg/kg to 1 mg/kg).

Formalin Licking Test

Male SD rats (80–100 g) are injected subcutaneously with a test compound dissolved in 0.1% methyl cellulose(MC)-saline or vehicle. After 30 min, 50 μl of a 2% formalin are injected into a hind paw. The number of licking the injected paw per observation period is measured from 15 to 30 min. after the injection of formalin and expressed as % inhibition compared to the respective vehicle group. This testing method is described in, for example, (1) R. L. Follenfant, et. al., Br. J. Pharmacol. 93, 85–92 (1988); (2) H. Rogers, et al., Br. J. Pharmacol. 106, 783–789 (1992); and (3) H. Wheeler-Aceto, et al., Psychopharmacology, 104, 35–44 (1991).

The compounds of Formula (I) of this invention can be administered by conventional pharmaceutical practice via either the oral, parenteral or topical routes to mammals, for the treatment of the indicated diseases. For administration to human patient by either route, the dosage is in the range of about 0.01 mg/kg to about 3000 mg/kg body weight of the patient per day, preferably about 0.01 mg/kg to about 1000 mg/kg body weight per day, more preferably about 0.1 mg/kg to about 100 mg/kg body weight per day administered singly or as a divided dose. However, variations will necessarily occur depending upon the weight and condition of the subject being treated, compound employed, the disease state being treated and the particular route of administration chosen.

The compounds of the present invention may be administered alone or in combination with pharmaceutically acceptable carriers by either of the above routes previously indicated, and such administration can be carried out in single or multiple doses. Generally, the compounds can be combined with various pharmaceutically acceptable carriers in the form of tablets, powders, capsules, lozenges, trochees, hard candies, powders, sprays, creams, salves, suppositories, jellies, gels, pastes, lotions, ointments, suspensions, solutions, elixirs, syrups or the like. Such pharmaceutical carriers include solvents, excipients, coating agents, bases, binders, lubricants, disintegrants, solubilizing agents, suspending agents, emulsifying agents, stabilizers, buffering agents, tonicity agents, preservatives, flavorating agents, aromatics, coloring agents and the like.

For example, the tablets can contain various excipients such as starch, lactose, glucose, microcrystalline cellulose, calcium sulfate, calcium carbonate, talc, titanium oxide and the like, coating agents such as gelatin, hydroxypropylcellulose and the like. binding agents such as gelatin, gum arabic, methylcellulose and the like, and the disintegrating agents such as starch, agar, gelatine, sodium hydrogencarbonate and the like. Additionally, lubricating agents such as magnesium stearate and talc are often very useful for tabletting purposes. Solid compositions of a similar type may also be employed as fillers in gelatine capsules; preferred materials in this connection also include lactose as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with diluents such as water, ethanol, propylene glycol, glycerin and various like combinations thereof.

In general, the therapeutically-effective compounds of this invention are present in such oral dosage forms at concentration levels ranging 5% to 70% by weight, preferably 10% to 50% by weight.

The compounds of the present invention in the form of a solution may be injected parenterlly such as intradermaly, subcutaneously, intravenously or intramuscularly. For example the solutions are sterile aqueous solutions, aqueous suspensions and an edible oil solutions. The aqueous solutions may be suitably buffered (preferably pH>8), and may contain enough salts or glucose to make the solution isotonic with blood. The aqueous solutions are suitable for intravenous injection purposes. The aqueous suspensions may contain a suitable dispersing or suspending agents such as sodium carboxymethylcellulose, methylcellulose, polyvinylpyrrolidone or gelatin. The aqueous suspensions can be used for subcutaneous or intramuscular injections. The edible oil such as cottonseed oil, sesame oil, coconut oil or peanut oil can be employed for the edible oil solutions. The oil solutions are suitable for intra-articular, intramuscular and subcutaneous injection. The preparation of all these solutions under sterile conditions is readily accomplished by standard pharmaceutical techniques well-known to those skilled in the art.

It is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATION

The present invention is illustrated by the following examples and preparation. However, it should be understood that the invention is not limited to the specific details of these examples and preparations. Melting points were taken with a Buchi micro melting point apparatus and is not corrected. Infrared Ray absorption spectra (IR) were measured by a Shimadzu infrared spectrometer (IR-470). $^1$H and $^{13}$C nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet. t, triplet; m, multiplet; br, broad.

Preparation 1
1-[4-(2-Oxo-2,3-dihydro-1H-1,3-benzimidazol-1-yl) piperidino]-1-cyclohexanecarbonitrile To a stirred suspension of 4-(2-keto-1-benzimidazolinyl) piperidine (500 mg, 2.3 mmol) in 2N HCl(1.15 ml, 2.3 mmol) and water(0.5 ml) was added cyclohexanone(0.24 ml, 2.3 mmol) at 0° C. To this mixture was added a solution of KCN(156 mg, 2.4 mmol) in water(0.3 ml) all at once at room temperature. After 17 h stirring at room temperature, the precipitated white solid was collected by filtration, washed with water, and dried under vacuum at 50° C. for 1 h to afford 605 mg of white powder. As this included small amount of starting material amine, this was purified by column chromatography(silica gel: 130 g, CH$_2$Cl$_2$MeOH:30/1 to 20/1) to give 293 mg(39.3%) of white powder, mp199–201° C.

MS m/z (EI direct): 324(M$^+$), 298(M$^+$—CN).
$^1$H NMR (270 MHz, CDCl$_3$) δ9.41 (1H, br.s), 7.24–7.18 (1H, m), 7.13–7.03 (3H, m), 4.42–4.29 (1H, m), 3.36–3.27 (2H, m), 2.58–2.31 (4H, m), 2.24–2.12 (2H, ), 1.97–1.88 (2H, m), 1.86–1.75 (2H, m), 1.70–1.50 (5H, m), 1.40–1.24 (1H, m).

Example 1
1-[1-(1-Phenylcyclohexyl)-4-piperidinyl]-1,3-dihydro-2H-1,3-benzimidazol-2-one To a solution of phenylmagnesium bromide (3M solution in diethyl ether, 0.75 ml, 2.25 mmol) in THF (1 ml) was added a suspension of 1-[4-(2-oxo-2,3-dihydro-1H-1,3-benzimidazol-1-yl)piperidino]-1-cyclohexanecarbonitrile (230 mg, 0.71 mmol) in THF (2 ml) at 0° C. Then the reaction mixture was stirred at room temperature for 18 h. To the reaction mixture was added sat.NH$_4$Cl aq. solution (1 ml) followed by addition of water (5 ml). The white precipitate appeared was collected by filtration, washed faith water and CH$_2$Cl$_2$, and dried to give 75 mg (28.1%) of title compound. The filtrate of CH$_2$Cl$_2$ wash was concentrated to give 171 mg of title compound and the starting material mixture, which was purified by column chromatography (silica gel:30 g, CH$_2$Cl$_2$/MeOH:50/1 to 15/1) to give 60 mg(22.5%) of title compound as white powder.

MS m/z(EI direct): 375(M$^+$), 332, 297, 240, 216, 198, 91.
$^1$H NMR (270 MHz, CDCl$_3$) δ8.20 (1H, br.s), 7.40–7.20 (5H, m), 7.11–7.00 (4H, m), 4.10–4.00 (1H, m), 3.27–3.15 (2H, m), 2.39–2.25 (2H, m), 2.14–2.05 (4H, m), 1.82–1.69 (6H, m), 1.62–1.24 (4H, m).

This free amine (130 mg, 0.35 mmol) was converted to HCl salt by treating with HCl gas dissolved methanol (2 ml). After evaporation of the solvent, the resulting white amorphous solid was solidified by adding acetone to give white powder, which was collected by filtration to afford 110 mg of white powder, mp 240.5–242° C.

Anal. Calcd for C$_{24}$H$_{29}$N$_3$O.HCl.1.6H$_2$O: C,65.40; H, 7.59; N, 9.53. Found: C, 65.63; H, 7.81; N, 9.12.

Example 2
1-[1-(1-Benzylcyclohexyl)-4-piperidinyl]-1,3-dihydro-2H-1,3-benzimidazol-2one This was prepared according to the procedure described in Example 1 using benzylmagnesium bromide instead of phenylmagnesium bromide. Yield was 60%.

$^1$H NMR (270 MHz, CDCl$_3$) δ8.96 (1H, br.s), 7.30–7.04 (9H, m), 4.43–4.28 (1H, m), 3.30–3.15 (2H, m), 2.66 (2H, s), 2.50–2.30 (4H, m), 1.92–1.55 (8H, m), 1.44–1.00 (4H, m).

IR(KBr): 1676 cm$^{-1}$
This free amine was converted to hydrochloride salt, mp 255–258° C.

MS(ESI) m/z: 390(M+H)$^+$.
Anal. Calcd for C$_{25}$H$_{31}$ClN$_3$O.HCl.4H$_2$O: C,60.29; H, 8.09; N, 8.44. Found: C, 59.99; H, 7.51; N, 8.51.

Example 3
1-[1-(1-Methylcyclohexyl)-4-piperidinyl]-1,3-dihydro-2H-1,3-benzimidazol-2-one This was prepared according to the procedure described in Example 1 using methylmagnesium bromide instead of phenylmagnesium bromide. Yield was 73%.

IR(KBr): 3454, 3382, 1708 cm$^{-1}$
This free amine was converted to hydrochloride salt, mp 266–269° C.

$^1$H NMR (270 MHz, DMSOd$_6$) δ10.91 (1H, br.s), 9.95–9.80 (1H, m), 7.70–7.60 (1H, m), 7.05–6.97 (3H, m), 4.70–4.55 (1H, m), 3.73–3.65 (2H, m), 3.25–3.10 (2H, m), 2.95–2.75 (2H, m), 2.00–1.60 (9H, m), 1.50–1.35 (2H, m), 1.32 (3H, s), 1.25–1.03 (1H, m).

Anal. Calcd for C$_{19}$H$_{27}$N$_3$O.HCl.1.2H$_2$O: C,61.43; H, 8.25; N, 11.31. Found: C, 61.47; H, 8.61; N, 11.08.

Example 4
1-[1-(1-Vinylcyclohexyl)-4-piperidinyl]-1,3-dihydro-2H-1,3-benzimidazol-2-one This was prepared according to the procedure described in Example 1 using vinylmagnesium bromide instead of phenylmagnesium bromide. Yield was 43%.

$^1$H NMR (270 MHz, CDCl$_3$) δ8.73 (1H, br.s), 7.30–7.25 (1H, m), 7.11–7.03 (3H, m), 5.71 (1H, dd, J=10.9, 17.8 Hz), 5.23 (1H, d, J=11.0 Hz), 5.01 (1H, d, J=17.8 Hz), 4.35–4.20 (1H, m), 3.23–3.12 (2H, m), 2.45–2.15 (4H, m), 1.88–1.35 (12H, m).

IR(KBr): 3339, 1705 cm$^{-1}$

This free amine was converted to hydrochloride salt, mp 196–200° C.

Anal. Calcd for $C_{20}H_{27}N_3O \cdot HCl \cdot 1.2H_2O$: C, 61.20; H, 8.06; N, 10.70. Found: C, 60.99; H, 8.31; N, 10.31.

Example 5
1-{1-[1-(2-Thienyl)cyclohexyl]-4-piperidinyl}-1,3-dihydro-2H-1,3-benzimidazol-2-one This was prepared according to the procedure described in Example 1 using 2-thienylmagnesium bromide instead of phenylmagnesium bromide. Yield was 60%.

$^1$H NMR (270 MHz, CDCl$_3$) δ8.11 (1H, br.s), 7.26–7.20 (2H, m), 7.10–7.00 (4H, m), 6.86 (1H, dd, J=1.1, 3.5 Hz), 4.20–4.05 (1H, m), 3.25–3.15 (2H, m), 2.48–2.30 (2H, m), 2.20–1.70 (10H, m), 1.60–1.37 (4H, m).

IR(KBr): 3175, 1699 cm$^{-1}$

This free amine was converted to hydrochloride salt, mp 162–166° C.

Anal. Calcd for $C_{22}H_{27}N_3OS \cdot HCl \cdot 0.3CH_3OH$: C, 62.64; H, 6.88; N, 9.83. Found: C, 62.47; H, 6.49; N, 9.91.

Example 6
1-{1-[1-(1-Ethynyl)cyclohexyl]-4-piperidinyl}-1,3-dihydro-2H-1,3-benzimidazol-2-one This was prepared according to the procedure described in Example 1 using ethynylmagnesium bromide instead of phenylmagnesium bromide. Yield was 29%.

$^1$H NMR (270 MHz, CDCl$_3$) δ8.69 (1H, br.s), 7.33–7.25 (1H, m), 7.10–7.00 (3H, m), 4.42–4.30 (1H, m), 3.29–3.20 (2H, m), 2.51–2.30 (4H, m), 2.36 (1H, s), 2.05–1.20 (12H, m).

IR(KBr): 3200, 2110, 1693 cm$^{-1}$

This free amine was converted to hydrochloride salt, mp 97–101° C.

Anal. Calcd for $C_{20}H_{25}N_3O \cdot HCl \cdot 0.5CH_3OH$: C, 65.50; H, 7.51; N, 11.18. Found: C, 65.67; H, 7.52; N, 11.32.

Example 7
1-[1-(1-Propylcyclohexyl)-4-piperidinyl]-1,3-dihydro-2-H-1,3-benzimidazol-2-one This was prepared according to the procedure described in Example 1 using propylmagnesium bromide instead of phenylmagnesium bromide. Yield was 53.3%.

$^1$H NMR (270 MHz, CDCl$_3$) δ9.25 (1H, br.s), 7.30–7.23 (1H, m), 7.12–7.00 (3H, m), 4.40–4.25 (1H, m), 3.20–3.05 (2H, m), 2.41–2.22 (4H, m), 1.85–1.55 (8H, m), 1.45–1.20 (8H, m), 0.90 (3H, t, J=6.5 Hz).

IR(KBr): 3175, 1686 cm$^{-1}$

This free amine was converted to hydrochloride salt, mp 185–189° C.

Anal. Calcd for $C_{21}H_{31}N_3O \cdot HCl \cdot 0.8CH_3OH$: C, 62.11; H, 8.89; N, 9.97. Found: C, 61.86; H, 8.54; N, 10.20.

Example 8
1-{1-[1-(4-Chlorophenyl)cyclohexyl]-4-piperidinyl}-1,3-dihydro-2H-1,3-benzimidazol-2-one This was prepared according to the procedure described in Example 1 using 4-chlorophenylmagnesium bromide instead of phenylmagnesium bromide. Yield was 3.6%.

$^1$H NMR (270 MHz, CDCl$_3$) δ8.55 (1H, br.s), 7.33 (2H, d, J=8.7 Hz), 7.26 (2H, d, J=8.7 Hz), 7.26–7.18 (1H, m), 7.10–7.02 (3H, m), 4.14–3.99 (1H, m), 3.24–3.14 (2H, m), 2.43–2.26 (2H, m), 2.10–2.00 (4H, m), 1.83–1.25 (10H, m).

IR(KBr): 3350, 1690 cm$^{-1}$

This free amine was converted to hydrochloride salt, mp 237–241° C.

Anal. Calcd for $C_{24}H_{28}ClN_3O \cdot HCl \cdot 3.2H_2O$: C, 57.19; H, 7.08; N, 8.34. Found: C, 56.85; H, 6.62; N, 7.94.

Example 9
1-{1-[1-(4-Methoxyphenyl)cyclohexyl]-4-piperidinyl}-1,3-dihydro-2H-1,3-benzimidazol-2-one This was prepared according to the procedure described in Example 1 using 4-methoxyphenylmagnesium bromide instead of phenylmagnesium bromide. Yield was 7.7%.

1H NMR (270 MHz, CDCl$_3$) δ9.03 (1H, br.s), 7.30–7.20 (3H, m), 7.10–7.00 (3H, m), 6.90 (2H, d, J=8.1 Hz), 4.15–4.00 (1H, m), 3.84 (3H, s), 3.27–3.15 (2H, m), 2.45–2.25 (2H, m), 2.20–1.96 (4H, m), 1.90–1.25 (10H, m).

IR(KBr): 1693 cm$^{-1}$

This free amine was converted to hydrochloride salt, mp 193–197° C.

Anal. Calcd for $C_{25}H_{31}N_3O_2 \cdot HCl \cdot 0.9CH_2Cl_2$: C, 60.00; H, 6.57; N, 8.11. Found: C, 59.73; H, 6.91; N, 7.83.

Preparation 2
1-Methyl-1-[4-(2oxo-2,3-dihydro-1H-1,3-benzimidazol-1-yl)piperidino]-ethyl cyanide This was prepared according to the procedure described in Preparation 1 using acetone instead of cyclohexanone. Yield was 63%.

$^1$H NMR (270 MHz, CDCl$_3$) δ9.16 (1H, br.s), 7.25–7.18 (1H, m), 7.13–7.03 (3H, m), 4.43–4.29 (1H, m), 3.33–3.24 (2H, m), 2.60–2.31 (4H, m), 1.98–1.87 (2H, m), 1.57 (6H, s).

IR(KBr): 3124, 2216, 1682 cm$^{-1}$

Anal. Calcd for $C_{16}H_{20}N_4O \cdot HCl \cdot 1.5H_2O$: C, 55.25; H, 6.95; N, 16.11. Found: C, 55.13; H, 6.71; N, 15.94.

Example 10
1-[1-(1-Methyl-1-phenylethyl)-4-piperidinyl]-1,3-dihydro-2H-1,3-benzimidazol-2-one This was prepared according to the procedure described in Example 1 using 2,2-dimethyl-2-[4-(2-keto-1-benzimidazolinyl)piperidinyl]acetonitrile and phenylmagnesium bromide. Yield was 59%.

$^1$H NMR (270 MHz, CDCl$_3$) δ8.40 (1H, br.s), 7.63–7.58 (1H, m), 7.37–7.19 (4H, m), 7.14–7.06 (3H, m), 4.35–4.25 (1H, m), 3.05–2.95 (2H, m), 2.50–2.24 (4H, m), 1.83–1.75 (2H, m), 1.39 (6H. s).

IR(KBr): 3449, 1686 cm$^{-1}$

MS m/z (EI direct): 335(M$^+$), 320(M$^+$—CH$_3$), 258, 216.

This free amine was converted to hydrochloride salt, mp 219–222° C.

Anal. Calcd for $C_{21}H_{25}N_3O \cdot HCl \cdot CH_3COCH_3$: C, 64.31; H, 7.31; N, 9.37. Found: C, 64.52; H, 7.21; N, 9.16.

Example 11
1-[1-(1,1-Dimethyl-2-phenylethyl)-4-piperidinyl]-1,3-dihydro-2H-1,3-benzimidazol-2-one This was prepared according to the procedure described in Example 10 using benzylmagnesium bromide instead of phenylmagnesium bromide. Yield was 73%.

$^1$H NMR (270 MHz, CDCl$_3$) δ9.71 (1H, br.s), 7.34–7.19 (6H, m), 7.15–7.04 (3H, m), 4.48–4.32 (1H, m), 3.40–3.25 (2H, m), 2.77 (2H, s), 2.50–2.32 (4H, m), 1.94–1.82 (2H, m), 1.06 (6H, s).

IR(KBr): 3387, 1701 cm$^{-1}$

MS m/z (EI direct): 349(M$^+$), 334(M$^+$—CH$_3$), 258, 201.

This free amine was converted to hydrochloride salt, mp 287–290° C.

Anal. Calcd for $C_{22}H_{27}N_3O \cdot HCl \cdot H_2O \cdot CH_3COCH_3$: C, 64.99; H, 7.85; N, 9.09. Found: C, 65.30: H, 8.07. N, 9.01.

Example 12
1-{1-[1-Methyl-1-(2-thienyl)ethyl]-4-piperidinyl}-1,3-dihydro-2H-1,3-benzimidazol-2-one This was prepared according to the procedure described in Example 10 using thienylmagnesium bromide instead of phenylmagnesium bromide. Yield was 100%.

hu 1H NMR (270 MHz, CDCl$_3$) δ9.10 (1H, br.s), 7.35–7.30 (1H, m), 7.20 (1H, dd, J=1.2, 5.1 Hz), 7.13–7.01 (3H, m), 6.91 (1H, dd, J=3.6, 5.1 Hz), 6.87 (1H, dd, J=1.2, 3.6 Hz), 4.42–4.28 (1H, m), 3.18–3.09 (2H, m), 2.50–2.22 (4H, m), 1.85–1.75 (2H, m), 1.49 (6H, s).

MS m/z (EI direct): 341($M^+$), 326($M^+$—$CH_3$), 258, 216.

This free amine was converted to hydrochloride salt, mp 274° C.

IR(KBr): 1686 cm$^{-1}$

Anal. Calcd for $C_{19}H_{23}N_3O.HCl.0.7H_2O$: C,58.43; H, 6.56; N, 10.76. Found: C, 58.12; H, 6.82; N, 10.56.

Example 13
1-{1-[1-(4-Fluorophenyl)-1-methylethyl]-4-piperidinyl}-1,3dihydro-2H-1,3-benzimidazol-2-one This was prepared according to the procedure described in Example 10 using 4-fluorophenylmagnesium bromide instead of phenylmagnesium bromide. Yield was 60%.

$^1$H NMR (270 MHz, CDCl$_3$) δ8.96 (1H, br.s), 7.56 (2H, dd, J=5.6, 8.7 Hz), 7.32–7.27 (1H, m), 7.14–6.97 (5H, m, including 2H, dd, J=8.7, 8.7 Hz at 7.01 ppm), 4.35–4.25 (1H, m), 3.02–2.93 (2H, m), 2.43–2.23 (4H, m), 1.83–1.74 (2H, m), 1.37 (6H, s).

IR(KBr): 1724 cm$^{-1}$

MS m/z (EI direct): 353($M^+$), 338($M^+$—$CH_3$), 258, 216.

This free amine was converted to hydrochloride salt, mp 246° C.

Anal. Calcd for $C_{21}H_{24}FN_3O.HCl.H_2O.1/6C_6H_6$: C,62.78; H, 6.70; N, 9.98. Found: C, 63.07; H, 6.58; N, 9.81.

Example 14
1-{1-[1-Methyl-1-(4-methylphenyl)ethyl]-4-piperidinyl}-1,3-dihydro-2H-1,3-benzimidazol-2-one This was prepared according to the procedure described in Example 10 using 4-tolylmagnesium bromide instead of phenylmagnesium bromide. Yield was 29%.

$^1$H NMR (270 MHz, CDCl$_3$) δ10.34 (1H, br.s), 7.48 (2H, d, J=8.2 Hz), 7.34–7.29 (1H, m), 7.19–7.05 (5H, m), 4.40–4.25 (1H, m), 3.05–2.95 (2H, m), 2.49–2.23 (4H, m), 2.34 (3H, s), 1.83–1.73 (2H, m), 1.38 (6H, s).

IR(KBr): 3230, 1682 cm$^{-1}$

MS m/z (EI direct): 349($M^+$), 334($M^+$—$CH_3$), 258, 216.

This free amine was converted to hydrochloride salt, mp 224–227° C.

Anal. Calcd for $C_{22}H_{27}N_3O.HCl.1.5H_2O.1/3C_6H_6$: C,65.66; H, 7.58; N, 9.57. Found: C, 65.32; H, 7.55; N, 9.78.

Example 15
1-[1-(1,1-Dimethyl-3-phenylpropyl)-4-piperidinyl]-1,3-dihydro-2H-1,3-benzimidazol-2-one This was prepared according to the procedure described in Example 10 using phenylethylmagnesium bromide instead of phenylmagnesium bromide. Yield was 34%.

$^1$H NMR (270 MHz, CDCl$_3$) δ10.44 (1H, br.s), 7.32–7.00 (9H, m), 4.42–4.28 (1H, m), 3.23–3.14 (2H, m), 2.76–2.66 (2H, m), 2.52–2.26 (4H, m), 1.91–1.82 (2H, m), 1.80–1.70 (2H, m), 1.13 (6H, s).

IR(KBr): 3125, 1697 cm$^{-1}$

MS m/z (EI direct): 363($M^+$), 348($M^+$—$CH_3$), 258.

This free amine was converted to hydrochloride salt, mp 290° C.

Anal. Calcd for $C_{23}H_{29}N_3O.HCl.0.5H_2O$: C,67.55; H, 7.64; N, 10.27. Found: C, 67.74; H, 7.82; N, 10.07.

Example 16
1-{1-[1-(4-Methoxyphenyl)-1-methylethyl]-4-piperidinyl}-1,3-dihydro-2H-1,3-benzimidazol-2-one This was prepared according to the procedure described in Example 10 using 4-methoxyphenylmagnesium bromide instead of phenylmagnesium bromide. Yield was 69%.

$^1$H NMR (270 MHz, CDCl$_3$) δ8.86 (1H, br.s), 7.50 (2H, d, J=8.7Hz), 7.33–7.28 (1H, m), 7.13–7.04 (3H, m), 6.87 (2H, d, J=8.9 Hz), 4.35–4.25 (1H, m), 3.81 (3H, s), 3.04–2.95 (2H, m), 2.42–2.21 (4H, m), 1.82–1.73 (2H, m), 1.37 (6H, s).

IR(KBr): 3105, 1699 cm$^{-1}$

MS m/z (EI direct): 365($M^+$), 350($M^+$—$CH_3$), 216.

This free amine was converted to hydrochloride salt, mp 208–212° C.

Anal. Calcd for $C_{23}H_{29}N_3O.HCl.0.5H_2O$: C,64.30; H, 7.11; N, 10.23. Found: C, 64.49; H, 7.34; N, 9.97.

Preparation 3
1-[4-(2-Oxo-2,3-dihydro-1H-1,3-benzimidazol-1-yl)piperidino]-1-cycloheptanecarbonitrile This was prepared according to the procedure described in Preparation 1 using cycloheptanone instead of cyclohexanone. Yield was 99%.

$^1$H NMR (270 MHz, CDCl$_3$) δ9.32 (1H, br.s), 7.25–7.00 (4H, m), 4.45–4.25 (1H, m), 3.28–3.16 (2H, m), 2.60–2.28 (4H, m), 2.26–2.10 (2H, m), 2.05–1.85 (4H, m), 1.80–1.40 (8H, m).

MS m/z (EI direct): 338($M^+$), 311, 283, 177.

IR(KBr): 3375, 2214, 1697 cm$^{-1}$

Example 17
1-[1-(1-Phenylcycloheptyl)-4-piperidinyl]-1,3-dihydro-2H-1,3-benzimidazol-2-one This was prepared according to the procedure described in Example 1 using phenylmagnesium bromide and 1-[4-(2-oxo-2,3-dihydro-1H-1,3-benzimidazol-1-yl)piperidino]-1-cycloheptanecarbonitrile. Yield was 56%.

$^1$H NMR (270 MHz, DMSOd$_6$) δ10.80 (1H, br.s), 7.55–7.45 (2H, m), 7.40–7.30 (2H, m), 7.25–7.15 (2H, m), 7.02–6.92 (3H, m), 4.10–3.95 (1H, m), 2.95–2.80 (2H, 2.30–1.90 (8H, m), 1.80–1.35 (10H, m).

MS m/z (EI direct): 389($M^+$), 332, 312, 304, 254, 216.

This free amine was converted to hydrochloride salt, mp 184° C.

IR(KBr): 3394, 1697 cm$^{-1}$

Anal. Calcd for $C_{25}H_{31}N_3O.HCl.1.3H_2O$: C,66.81; H, 7.76; N, 9.35. Found: C, 66.92; H, 7.59; N, 9.29.

Example 18
1-{1-[1-(2-Thienyl)cycloheptyl]-4-piperidinyl}-1,3-dihydro-2H-1,3-benzimidazol-2-one This was prepared according to the procedure described in Example 21 using thienylmagnesium bromide instead of phenylmagnesium bromide. Yield was 81%.

$^1$H NMR (270 MHz, CDCl$_3$) δ8.77 (1H, br.s), 7.26–7.19 (2H, m), 7.10–7.00 (3H, m), 6.97–6.88 (2H, m), 4.32–4.18 (1H, m), 3.16–3.05 (2H, m), 2.45–2.10 (6H, m), 2.05–1.90 (2H, m), 1.85–1.50 (10H, m).

IR(KBr): 3188, 1707 cm$^{-1}$

MS m/z (EI direct): 395($M^{30}$), 338, 312, 261, 216.

This free amine was converted to hydrochloride salt, mp 175° C.

Anal. Calcd for $C_{23}H_{29}N_3OS.HCl.1.5H_2O$: C,60.18; H, 7.25; N, 9.15. Found: C, 60.55; H, 6.85; N, 9.54.

Preparation 4

1-Ethyl-1-[4-(2-oxo-2,3-dihydro-1H-1,3-benzimidazol-1-yl)piperidino]-propyl cyanide This was prepared according to the procedure described in Preparation 1 using 3pentanone instead of cyclohexanone. Yield was 24%.

$^1$H NMR (270 MHz, CDCl$_3$) δ9.14 (1H, br.s), 7.25–7.15 (1H, m), 7.15–7.05 (3H, m), 4.45–4.30 (1H, mn), 3.28–3.18 (2H, m), 2.58–2.32 (4H, m), 2.00–1.70 (6H, m), 1.04 (6H, t, J=7.4Hz).

MS m/z (EI direct): 312(M$^+$), 283, 256, 244, 216.

Example 19

1-[1-(1-Ethyl-1-phenylpropyl)-4-piperidinyl]-1,3-dihydro-2H-1,3-benzimidazol-2-one This was prepared according to the procedure described in Example 1 using 1-ethyl-1-[4-(2-oxo-2,3-dihydro-1H-1,3-benzimidazol-1-yl)piperidino]-propyl cyanide and phenylmagnesium bromide. Yield was 62%.

$^1$H NMR (270 MHz, CDCl$_3$) δ8.79 (1H, br.s), 7.50–7.40 (2H, m), 7.40–7.17 (4H, m), 7.15–7.00 (3H, m), 4.35–4.20 (1H, m), 3.25–3.10 (2H, m), 2.45–2.25 (4H, m), 2.05–1.85 (4H, m), 1.85–1.70 (2H, m), 0.84 (6H, t J=7.4 Hz).

MS m/z (EI direct): 363(M$^+$), 334(M$^+$—C$_2$H$_5$), 216.

This free amine was converted to hydrochloride salt, mp 229° C.

IR(KBr): 3402, 3126, 1692 cm$^{-1}$

Anal. Calcd for C$_{23}$H$_{29}$N$_3$O.HCl.1.5H$_2$O: C,64.70; H, 7.79; N, 9.84. Found: C, 64.86; H, 7.62; N, 10.09.

Example 20

1-{1-[1-Ethyl-1-(2-thienyl)propyl]-4-piperidinyl}-1,3-dihydro-2H-1,3-benzimidazol-2-one This was prepared according to the procedure described in Example 23 using 2-thienylmagnesium bromide instead of phenylmagnesium bromide. Yield was 90%.

$^1$H NMR (270 MHz, CDCl$_3$) δ9.68 (1H, br.s), 7.31–7.26 (1H, m), 7.20 (1H, dd, J=1.1, 5.1 Hz), 7.13–7.00 (3H, m), 6.96 (1H, dd, J=3.6, 5.1 Hz), 6.82 (1H, dd, J=1.2, 3.5 Hz), 4.35–4.20 (1H, m), 3.30–3.19 (2H, m), 2.48–2.21 (4H, m), 2.07–1.87 (4H, m), 1.83–1.73 (2H, m), 0.89 (6H, t, J=7.4 Hz).

MS m/z (EI direct): 340(M$^+$—C$_2$H5), 216.

This free amine was converted to hydrochloride salt, mp 182° C.

IR(KBr): 3400. 3200, 1699 cm$^{-1}$

Anal. Calcd for C$_{23}$H$_{29}$N$_3$OS.HCl.1.5H$_2$O.0.5C$_6$H$_6$: C,58.75; H, 7.22; N, 9.56. Found: C, 58.93; H, 6.89; N, 9.20.

Preparation 5

1-[4-(2-Oxo-2,3-dihydro-1H-1,3-benzimidazol-1-yl)piperidino]-1-cyclobutanecarbonitrile This was prepared according to the procedure described in Preparation 1 using cyclobutanone instead of cyclohexanone. Yield was 71%.

$^1$H NMR (270 MHz, CDCl$_3$) δ9.50 (1H, br.s), 7.26–7.18 (1H, m), 7.15–7.05 (3H, m), 4.43–4.28 (1H, m), 2.99–2.89 (2H, m), 2.60–2.40 (4H, m), 2.36–2.10 (5H, m), 2.00–1.85 (3H, m).

MS m/z (EI direct): 296(M$^+$), 269, 163, 134.

Example 21

1-[1-(1-Phenylcyclobuyl)-4-piperidinyl]-1,3-dihydro-2H-1,3-benzimidazol-2-one

This was prepared according to the procedure described in example 1 using 1-[4-(2-oxo-2,3-dihydro-1H-1,3-benzimidazol-1-yl)piperidino]-1-cyclobutanecarbonitrile and phenylmagnesium bromide. Yield was 48%.

$^1$H NMR (270 MHz, CDCl$_3$) δ9.30 (1H, br.s), 7.42–7.24 (6H, m), 7.10–7.00 (3H, m), 4.10–3.94 (1H, m), 3.08–2.97 (2H, m), 2.55–2.28 (6H, m), 2.01–1.55 (6H, m).

IR(KBr): 3184, 3136, 1686 cm$^{-1}$

MS m/z (EI direct): 347(M$^+$), 318(M$^+$—C$_2$H$_5$), 304, 212, 184.

This free amine was converted to hydrochloride salt, mp 278° C.

Anal. Calcd for C$_{22}$H$_{25}$N$_3$O.HCl.0.2H$_2$O.0.3CH$_2$Cl$_2$: C,64.85; H, 6.59; N, 10.17. Found: C, 65.01; H, 6.51; N, 10.19.

Example 22

1-{1-[1-(2-Thienyl)cyclobuyl]-4-piperidinyl}-1,3-dihydro-2H-1,3-benzimidazol-2-one This was prepared according to the procedure described in example 25 using 2-thienylmagnesium bromide instead of phenylmagnesium bromide. Yield was 84%.

$^1$H NMR (270 MHz, CDCl$_3$) δ9.82 (1H, br.s), 7.31–7.23 (2H, m), 7.12–7.01 (4H, m), 6.96–6.92 (1H, m), 4.20–4.06 (1H, m), 3.04–2.94 (2H, m), 2.55–2.30 (6H, m), 2.05–1.70 (6H, m).

IR(KBr): 3179, 1686 cm$^{-1}$

MS m/z (EI direct): 353(M$^+$), 320, 219, 191.

This free amine was converted to hydrochloride salt. mp 250° C.

Anal. Calcd for C$_{20}$H$_{23}$N$_3$OS.HCl.0.5H$_2$O: C,60.21; H, 6.32; N, 10.53. Found: C, 60.34; H, 6.09: N, 10.29.

Preparation 6

1-(1-Phenylcyclopentyl)piperidin-4one

This was prepared according to the procedure of B. de Costa et al(*J.Chem.Soc.Perkin Trans.* 1, 1992, 1671) using 1-phenylcyclopentylamine(*Organic Syntheses,* VI, 910) instead of 1-(2-benzo[b]thienyl)cyclohexylamine. Yield was 24.7%.

$^1$H NMR (270 MHz, CDCl$_3$) δ7.33–7.15 (5H, m), 2.57 (4H, dd, J=5.9, 6.1 Hz), 2.31 (4H, dd, J=5.9, 6.1 Hz), 2.18–1.95 (4H, m), 1.80–1.65 (2H, m), 1.60–1.40 (2H, m).

MS m/z (EI direct): 243(M$^+$), 221, 158, 135.

Preparation 7

N-(2-Nitrophenyl)-N-[1-(1-phenylcyclopentyl)-4-piperidinyl]amine

This was prepared according to the procedure of B. de Costa et al(*J.Chem.Soc.Perkin Trans.* 1, 1992, 1671) using 1-(1-phenylcyclopentyl)piperidin-4-one and the procedure of N. A. Meanwell et al(*Bioorg. Med. Chem. Lett.,* 1996, 6, 1641). Total yield was 89%.

$^1$H NMR (270 MHz, CDCl$_3$) δ8.13 (1H, dd, J=1.3, 8.7 Hz), 8.02 (1H, br.d, J=6.8 Hz), 7.40–7.23 (6H, m), 6.74 (1H, d, J=8.6 Hz), 6.57 (1H, dd, J=7.6, 8.1 Hz), 3.38–3.22 (1H, m), 3.02–2.90 (2H, m), 2.25–1.90 (8H, m), 1.85–1.40 (6H, m).

MS m/z (EI direct): 365(M$^+$), 336, 288, 244.

Example 23

1-[1-(1-Phenylcyclopentyl)-4-piperidinyl]-1,3-dihydro-2H-1,3-benzimidazol-2-one

This was prepared according to the procedure of N. A. Meanwell et al(*Bioorg. Med.Chem. Lett.,* 1996, 6, 1641) using N-(2-nitrophenyl)-N-[1-(1-phenylcyclopentyl)-4-piperidyl]amine. Total yield was 91%.

$^1$H NMR (270 MHz, CD$_3$OD+CDCl$_3$) δ7.50–7.30 (6H, m), 7.15–7.03 (3H, m), 4.16–4.02 (1H, m), 3.32–3.17 (2H, m), 2.66–2.37 (4H, m), 2.17–1.98 (4H, m), 1.9–1.70 (4H, m), 1.54–1.42 (2H, m).

IR(KBr): 3310, 1686 cm$^1$

MS m/z (EI direct): 361(M), 332, 304, 284, 227, 216, 198, 82.

This free amine was converted to hydrochloride salt, mp 229° C.

Anal. Calcd for $C_{23}H_{27}N_3O \cdot HCl \cdot 1.3CH_2Cl_2$: C,54.71; H, 6.07; N, 8.27. Found: C, 57.36; H, 6.00; N, 8.32.

Example 24
1-[1-(1-Phenylcyclohexyl)-4-piperidinyl]-1,3-dihydro-2H-6-chloro-1,3-benzimidazol-2-one This was prepared according to the procedure of N. A. Meanwell et al(*Bioorg. Med.Chem. Lett.*, 1996, 6, 1641) and U.S. patent (U.S. Pat. No. 5,124,457). Total yield was 11% from 1-(1-phenylcyclohexyl)piperidin-4-one.

$^1$H NMR (270 MHz, CDCl$_3$) δ8.86 (1H, br.s), 7.40–7.20 (5H, m), 7.02–6.91 (3H, m), 4.05–3.94 (1H, m), 3.26–3.21 (2H, m), 2.33–2.04 (4H, m), 1.79–1.38 (12H, m).

MS m/z (EI direct): 409(M$^+$), 366, 338, 250, 198, 91.

IR(KBr): 3400, 1699 cm$^{-1}$

This free amine was converted to hydrochloride salt, mp 199–201° C.

Anal. Calcd for $C_{24}H_{28}ClN_3O \cdot HCl \cdot 2H_2O$: C,59.75; H, 6.89; N, 8.71. Found: C, 59.56; H, 6.49; N, 8.76.

Preparation 8
1-(1-Phenylcycloheptyl)piperidin-4-one

This was prepared according to the procedure of B. de Costa et al(*J.Chem.Soc.Perkin Trans.* 1, 1992, 1671) using 1-phenylcycloheptylamine (E. J. Cone et al, *J. Med.Chem.*, 1981, 1429) instead of 1-(2-benzo[b]thienyl)cyclohexylamine. Yield was 39.4%

1H NMR (270 MHz, CDCl$_3$) δ7.52–7.46 (2H, m), 7.35–7.18 (3H, m), 2.74 (4H, t, J=5.9 Hz), 2.30 (4H, t, J=5.9 Hz), 2.11–2.06 (4H, m), 1.78–1.47 (8H, m).

MS m/z (EI direct): 271(M$^+$).

Preparation 9
N-(5-Chloro-2-nitrophenyl)-N-[1-(1-phenylcycloheptyl)-4-piperidinyl]amine This was prepared according to the procedure of B. de Costa et al(*J.Chem.Soc.Perkin Trans.* 1, 1992, 1671) using 1-(1-phenylcycloheptyl)piperidin-4-one and the procedure of N. A. Meanwell et al(*Bioorg. Med.Chem. Lett.*, 1996, 6, 1641) using 4-chloro-2-fluoronitrobenzene. Total yield was 53%.

$^1$H NMR (270 MHz, CDCl$_3$) δ8.20–8.05 (2H, m, including 1H, d, J=9.2 Hz at 8.10 ppm), 7.48–7.17 (5H, m), 6.78 (1H, d, J=2.3 Hz), 6.55 (1H, dd, J=2.3, 9.2 Hz), 3.45–3.31 (1H, m), 2.83–2.78 (2H, m), 2.33–2.23 (2H, m), 2.08–2.04 (4H, m), 1.98–1.92 (2H, m), 1.79–1.71 (2H, m), 1.52–1.47 (8H, m).

MS m/z (EI direct): 427(M$^+$).

Example 25
1-[1-(1-Phenylcycloheptyl)-4-piperidinyl]-1,3-dihydro-2H-6-chloro-1,3-benzimidazol-2-one This was prepared according to the procedure of N. A. Meanwell et al (*Bioorg. Med.Chem. Lett.*, 1996, 6, 1641) using N-(5-chloro-2-nitrophenyl)-N-[1-(1-phenylcycloheptyl)-4-piperidinyl]amine. Total yield was 82.8%.

$^1$H NMR (270 MHz, CDCl$_3$) δ9.90 (1H, br.s), 7.53–7.49 (2H, m), 7.37–7.20 (4H, m), 7.05–6.97 (2H, m), 4.24–4.13 (1H, m), 2.99–2.95 (2H, m), 2.31–2.03 (8H, m), 1.78–1.47 (10H, m).

MS m/z (EI direct): 423(M$^+$), 366, 338, 250, 91.

This free amine was converted to hydrochloride salt, mp 191–195° C.

IR(KBr): 3261, 1705 cm$^{-1}$

Anal. Calcd for $C_{25}H_{30}ClN_3O \cdot HCl \cdot 0.5H_2O$: C,63.96; H, 6.87; N, 8.95. Found: C. 63.66; H, 6.95; N, 8.59.

Preparation 10
1-(1-Phenylcyclopropyl)piperidin-4-one

This was prepared according to the procedure of B. de Costa et al(*J.Chem.Soc.Perkin Trans.* 1, 1992, 1671) using 1-phenylcyclopropylamine (E. J. Cone et al, *J. Med.Chem.*. 1981, 1429) instead of 1-(2-benzo[b]thienyl)cyclohexylamine. Yield was 35%.

$^1$H NMR (270 MHz, CDCl$_3$) δ7.35–7.25 (5H, m), 2.81 (4H, t, J=6.1 Hz), 2.38 (4H, t, J=6.1 Hz). 1.07–1.01 (2H, m), 0.97–0.87 (2H, m).

MS m/z (EI direct): 215(M$^+$).

Preparation 11
N-(2-Nitrophenyl)-N-[1-(1-phenylcyclopropyl)-4-piperidinyl]amine This was prepared according to the procedure of B. de Costa et al(*J.Chem.Soc.Perkin Trans.* 1, 1992, 1671) using 1-(1-phenylcyclopropyl)piperidin-4-one and the procedure of N. A. Meanwell et al(*Bioorg. Med. Chem. Lett.*, 1996, 6, 1641). Total yield was 56%.

hu 1H NMR (270 MHz, CDCl$_3$) δ8.13 (1H, dd, J=1.6, 8.6 Hz), 7.99 (1H, br.d, J=7.4 Hz), 7.38–7.25 (6H, m), 6.73 (1H, br.d, J=8.2 Hz), 6.60–6.53 (1H, m), 3.36–3.21 (1H, m), 3.08–2.98 (2H, m), 2.23 (2H, ddd, J=2.3, 11.5, 11.5 Hz), 2.08–1.98 (2H, m), 1.64–1.48 (2H, m), 0.98–0.91 (2H, m), 0.89–0.82 (2H, m).

MS m/z (EI direct): 337(M$^+$).

Example 26
1-[1-(1-Phenylcyclopropyl)-4-piperidinyl]-1,3-dihydro-2H-1,3- benzimidazol-2-one This was prepared according to the procedure of N. A. Meanwell et al (*Bioorg. Med.Chem. Lett.*, 1996, 6, 1641). Total yield was 85%.

$^1$H NMR (270 MHz, CD$_3$OD+CDCl$_3$) δ7.40–7.30 (7H, m), 7.10–7.00 (3H, m), 4.18–4.03 (1H, m), 3.35–3.15 (2H, m), 2.60–2.20 (4H, m), 1.82–1.72 (2H, m), 1.20–0.90 (4H, m).

MS m/z (EI direct): 333(M$^+$), 304, 198.

This free amine was converted to hydrochloride salt, mp 258° C.

IR(KBr): 3177, 1688 cm$^{-1}$

Example 27
3-Methyl-1-[1-( 1-phenylcycloheptyl)-4-piperidinyl]-1,3-dihydro-2H-1,3-benzimidazol-2-one To a stirred suspension of 1-[1-(1-phenylcycloheptyl)-4-piperidyl]-1,3-dihydro-2H-1,3-benzimidazol-2-one (116 mg, 0.298 mmol) in DMF (1 ml) was added NaH (60% oil suspension, 18 mg, 0.447 mmol) at rt. After 30 min stirring at rt, iodomethane (22.3 μl, 0.358 mmol) was added to the reaction mixture at rt. After 15 min stirring at rt, the reaction mixture was diluted with CH$_2$Cl$_2$, washed with water and brine, dried (Na$_2$SO$_4$), filtered, and concentrated to give pale yellow solid, which was purified by column chromatography (silica gel:5 g, hexane/ethyl acetate:5/1–3/1) to give 83 mg (69%) of white solid.

1H NMR (270 MHz, CDCl$_3$) δ7.54 (2H, m), 7.36–7.28 (2H, m), 7.26–7.17 (2H, m), 7.10–7.03 (2H, m), 6.99–6.93 (1H, m), 4.32–4.14 (1H, m), 3.26–3.21 (2H, m), 3.38 (3H, s), 3.00–2.86 (2H, m), 2.34–2.20 (4H, m), 2.12–2.03 (4H, m), 1.84–1.42 (8H, m).

This free amine was converted to hydrochloride salt, mp 219–220° C.

IR(KBr): 3400, 1701 cm$^{-1}$

Anal. Calcd for $C_{26}H_{33}N_3O \cdot HCl \cdot 0.4H_2O$: C,69.83; H, 7.84; N, 9.40. Found: C, 70.03; H, 7.96; N, 9.50.

Preparation 12
1-(1-Phenylcycloheptyl)piperidin-4-one

This was prepared according to the procedure of Preparation 3 and Example 21 using 1,4-dioxa-8-azaspiro[4.5]decane hydrochloride instead of 4-(2-keto-1-benzimidazolinyl)-piperidine. Yield was 58%.

$^1$H NMR data was identical with the product data of Preparation 8.

Preparation 13
4-(2-Keto-5-methoxy-1-benzimidazolinyl)piperidine

A mixture of 2-chloro-5-methoxynitrobenzene (5.00 g, 26.6 mmol), 4-amino-1-benzylpiperidine (25.4 g, 133 mmol), $K_2CO_3$ (4.49 g, 32.5 mmol), and CuO (663 mg, 8.33 mmol) was stirred at 200° C. for 2 h. After cooling down to rt, the reaction mixture was diluted with $CH_2Cl_2$ (70 ml) and water (40 ml), and stirred at rt for 0.5 h. After filtration, the organic layer was separated and was washed with brine, dried ($Na_2SO_4$), filtered, and concentrated to give brown oil, which was purified by column chromatography (silica gel;400 g, hexane/ethyl acetate:3/1 to 2/1) to afford 1.17 g(13%) of orange color solid.

$^1$H NMR (270 MHz, CDCl$_3$) δ8.08 (1H, br.d, J=7.4 Hz), 7.61 (1H, d, J=3.0 Hz), 7.36–7.22 (5H, m), 7.12 (1H, dd, J=3.1, 9.4 Hz), 6.83 (1H, d, J=9.6 Hz), 3.79 (3H, s), 3.60–3.50 (1H, m), 3.54 (2H, s), 2.88–2.78 (2H, m), 2.30–2.18 (2H, m), 2.10–1.99 (2H, m), 1.75–1.60 (2H, m).

A mixture of the above nitrobenzene derivative (1.23 g, 3.61 mmol) and $SnCl_2$—$H_2O$ (4.07 g, 18 mmol) in EtOH (40 ml) was refluxed for 2 h. After evaporation of the solvent, the residue was diluted with $CH_2Cl_2$ (40 ml) and saturated aqueous $NaHCO_3$ solution (30 ml). The organic layer separated was washed with brine, dried (NaSO$_4$), filtered, and concentrated to give 1.19 g (quantitative yield) of brown oil. To a solution of this oil (1.19 g, 3.61 mmol) in benzene (50 ml) was added trichloromethyl chloroformate (0.51 ml, 4.24 mmol) at rt. Then the mixture was refluxed for 2 h. After cooling down to rt, the mixture was basified with saturated aqueous $NaHCO_3$ solution, extracted with ethyl acetate. The extract was washed with brine, dried (NaSO$_4$), filtered, and concentrated to give brown oil, which was purified by column chromatography (silica gel; 60 g, $CH_2Cl_2$/MeOH:30/1 to 20/1) to afford 1.04 g (85%) of pale brown color solid.

$^1$H NMR (270 MHz, CDCl$_3$) δ9.34 (1H, br.s), 7.40–7.23 (5H, m), 7.17 (1H, d, J=8.7 Hz), 6.70 (1H, d, J=2.5 Hz), 6.63 (1H, dd, J=2.5, 8.7 Hz), 4.40–4.26 (1H, m), 3.80 (3H, s), 3.58 (2H, s), 3.10–3.00 (2H, m), 2.55–2.35 (2H, m), 2.24–2.12 (2H, m), 1.85–1.75 (2H, m).

A mixture of the above benzimidazolinone derivative (0.54 g, 1.6 mmol) and 20%Pd(OH)$_2$/C (162 mg) in MeOH (10 ml) was stirred under hydrogen atmosphere at rt for 15 h. After removal of the catalyst by filtration, the filtrate was concentrated to give 387 mg (98%) of pale brown amorphous solid.

$^1$H NMR (270 MHz, DMSOd$_6$+CDCl$_3$) δ7.15 (1H, d, J=8.6 Hz), 6.67 (1H, d, J=2.3 Hz), 6.58 (1H, dd, J=2.5, 8.6 Hz), 4.46–4.30 (1H, m), 3.78 (3H, s), 3.32–3.23 (2H, m), 2.86–2.73 (2H, m), 2.44–2.26 (2H, m), 1.87–1.76 (2H, m).

Example 28
5-Methoxy-1-[1-(1-phenylcycloheptyl)-4-piperidinyl]-1,3-dihydro-2H-1,3-benzimidazol-2-one This was prepared according to the procedure of Preparation 3 and Example 21 using 4-(2-keto-5-methoxy-1-benzimidazolinyl)piperidine. Total yield was 66.4%.

$^1$H NMR (270 MHz, CDCl$_3$) δ9.40 (1H, br.s), 7.53–7.48 (2H, m), 7.36–7.17 (3H, m), 7.11 (1H, d, J=8.7 Hz), 6.69 (1H, d, J=2.5 Hz), 6.64 (1H, dd, J=2.5, 8.7 Hz), 4.30–4.15 (1H, m), 3.79 (3H, s), 3.00–2.90 (2H, m), 2.34–2.05 (8H, m), 1.85–1.45 (10H, m).

This free amine was converted to hydrochloride salt, mp 189–192° C.

IR(KBr): 3400, 1705 cm$^{-1}$

Anal. Calcd for $C_{26}H_{33}N_3O_2 \cdot HCl \cdot 0.7H_2O$: C,66.64; H, 7.61; N, 8.97. Found: C, 66.43; H, 7.58; N, 8.95.

Example 29
1-[1-(4,4-Dimethyl-1-Phenylcyclohexyl)-4-piperidinyl]-1,3-dihydro-2H-1,3-benzimidazol-2-one This was prepared according to the procedure of Preparation 1 and Example 1 using 4, 4-dimethylcyclohexanone (W. L. Meyer et al., *J. Org. Chem.*, 1985, 50, 438–447) instead of cyclohexanone. Total yield was 42%.

$^1$H NMR (270 MHz, CDCl$_3$) δ9.64 (1H, br.s), 7.40–7.20 (6H, m), 7.10–7.00 (3H, m), 4.16–4.00 (1H, m), 3.28–3.15 (2H, m), 2.46–2.27 (2H, m), 2.17–2.00 (4H, m), 1.90–1.48 (6H, m), 1.26–1.12 (2H, m), 1.04 (3H, s), 0.84 (3H, s).

MSm/z(EIdirect): 403(M$^+$), 333, 216, 198, 91.

This free amine was converted to hydrochloride salt, mp 256° C.

IR(KBr): 3400, 1701 cm$^{-1}$

Anal. Calcd for $C_{26}H_{33}N_3O \cdot HCl \cdot H_2O$: C,68.18; H, 7.92; N, 9.17. Found: C, 68.20; H, 8.19; N, 9.05.

Example 30
1-[4-Piperidinyl-1-(1-Propylcyclononyl)]-1,3-dihydro-2H-1,3-benzimidazol-2-one This was prepared according to the procedure of Preparation 1 and Example 1 using cyclononanone instead of cyclohexanone and propylmagnesium bromide instead of phenylmagnesium bromide. Total yield was 3.4%.

$^1$H NMR (270 MHz, CDCl$_3$) δ9.85 (1H, br.s), 7.30–7.00 (4H, m), 4.40–4.26 (1H, m). 3.24–3.14 (2H, m), 2.46–2.20 (4H, m), 1.83–1.60 (6H, m), 1.58–1.25 (16H, m), 0.89 (3H, br.t, J=4.9 Hz).

MSm/z(EIdirect): 383(M$^+$), 368, 354, 342, 298, 257.

This free amine was converted to hydrochloride salt, mp 185° C.

IR(KBr): 3400, 1686 cm$^{-1}$

Anal. Calcd for $C_{24}H_{37}N_3O \cdot HCl \cdot 0.75H_2O \cdot 0.25CH_2Cl_2$: C, 64.05; H, 8.87; N, 9.24. Found: C, 64.17; H, 8.64; N, 8.98.

Preparation 14
8-Amino-8-phenylbicyclo[4.3.0]nonan

This was prepared from cis-hexahydroindan-2-one (J. E. Starr, et al., *J Org. Chem.*, 1966, 31, 1393–1402) according to the procedure of E. J. Cone et al. (*J. Med. Chem.*, 1981, 24, 1429). Overall yield was 15.4%.

$^1$H NMR (270 MHz, CDCl$_3$) δ7.50–7.15 (5H, m), 2.42–4.25 (2H, m), 2.15–2.00 (2H, m), 1.95–1.85 (2H, m), 1.70–1.25 (10H, m).

MS m/z (EI direct): 215(M$^+$), 198, 172, 158, 104.

Preparation 15
1-(8-Phenylbicyclo[4.3.0]nonan-8-yl)piperidin-4-one

This was prepared from 8-amino-8-phenylbicyclo[4.3.0]nonan according to the procedure described in Preparation 6. Overall yield was 10%.

¹H NMR (270 MHz, CDCl₃) δ7.44–7.17 (5H, m), 2.64–2.55 (4H, m), 2.35–2.35 (4H, m), 2.31–2.15 (2H, m), 2.10–1.85 (2H, m), 1.60–1.20 (10H, m).

MS m/z (EI direct): 297(M⁺), 254, 240, 220, 200.

Example 31

1-[4-Piperidinyl-1-(8-phenylbicyclo[4.3.0]nonan-8-yl)]-1,3-dihydro-2H-1,3-benzimidazol-2-one This was prepared from 1-(8-phenylbicyclo[4.3.0]nonan-8-yl)piperidin4-one according to the procedure described in Preparation 7 and Example 27. Overall yield was 10%.

¹H NMR (270 MHz, CDCl₃) δ8.79 (1H, br.s), 7.44–7.00 (9H, m), 4.20–4.06 (1H, m), 3.16–3.00 (2H, m), 2.44–2.14 (4H, m), 2.05–1.10 (16H, m).

MS m/z (EI direct): 415(M⁺), 358, 338, 304, 280, 216, 82.

Preparation 16

1-(1-Phenylcyclooctyl)piperidin-4-one

This was prepared according to the procedure of Preparation 6 using 1-phenylcyclooctylamine(*J. Med. Chem.*, 1996, 6, 1614) instead of 1-phenylcyclopentylamine. Total yield from cyclooctanone was 9.3%.

¹H NMR (270 MHz, CDCl₃) δ7.45–7.18 (5H, m), 2.74 (4H, dd, J=5.8, 6.1 Hz), 2.32 (4H, dd, J=5.8, 6.1 Hz), 2.28–2.05 (4H, m), 1.80–1.30 (10H, m).

Preparation 17

N-(2-Nitrophenyl)-N-[1-(1-phenylcyclooctyl)-4-piperidinyl]amine

This was prepared according to the procedure of Preparation 7 using 1-(1-phenylcyclooctyl)piperidin4-one. Total yield was 76%.

¹H NMR (270 MHz, CDCl₃) δ8.14 (1H, dd, J=1.6, 8.7 Hz), 8.05 (1H, br.d, J=7.3 Hz), 7.44–7.18 (6H, m), 6.78 (1H, d, J=8.7 Hz), 6.60–6.53 (1H, m), 3.44–3.30 (1H, m), 3.02–2.90 (2H, m), 2.25–1.91 (8H, m), 1.85–1.40 (12H, m).

MS m/z (EI direct): 407(M⁺), 336, 91.

Example 32

1-[1-(1-Phenylcyclooctyl)-4piperidinyl]-1,3-dihydro-2H-1,3-benzimidazol-2-one

This was prepared according to the procedure of Example 23 using N-(2-Nitrophenyl)-N-[1-(1-phenylcyclooctyl)-4piperidinyl]amine. Total yield was 47%.

¹H NMR (270 MHz, CDCl₃) δ7.50–7.20 (7H, m), 7.15–7.00 (3H, m), 4.23–4.08 (1H, m), 3.20–3.10 (2H, m), 2.40–2.00 (8H, m), 2.00–1.30 (12H, m).

MS m/z (EI direct): 403(M⁺), 332, 304, 268, 216, 184, 82.

This free amine was converted to hydrochloride salt, mp 196° C.

IR(KBr): 3375, 1697 cm⁻¹

Anal. Calcd for $C_{26}H_{33}N_3O \cdot HCl \cdot 0.2CH_2Cl_2 \cdot H_2O$: C,66.25; H, 7.72; N, 8.85. Found: C, 66.38; H, 7.58; N, 8.92.

Example 33

1-[1-(1-Phenylcyclononyl)-4-piperidinyl]-1,3-dihydro-2H-1,3-benzimidazol-2-one

This was prepared according to the procedure of Preparation 16, 17, and Example 32 using cyclononane instead of cyclooctanone. Total yield was 4.2% from cyclononanone.

¹H NMR (270 MHz, CDCl₃) δ8.81 (1H, br.s), 7.50–7.03 (9H, m), 4.22–4.15 (1H, m), 3.25–3.15 (2H, m), 2.35–1.30 (22H, m).

MS m/z (EI direct): 417(M⁻¹), 374, 332, 304, 282, 216, 82.

This free amine was converted to hydrochloride salt, mp 187° C.

IR(KBr): 3404, 1697 cm⁻¹

Anal. Calcd for $C_{27}H_{35}N_3O \cdot HCl \cdot 0.5CH_2Cl_2$: C,65.69; H, 7.70; N, 8.67. Found: C, 66.07; H, 7.56; N, 8.64.

Example 34

1-[1-(1-Phenylcyclodecyl)-4-piperidinyl]-1,3-dihydro-2H-1,3-benzimidazol-2-one

This was prepared according to the procedure of Preparation 16, 17, and Example 32 using cyclodecanone instead of cyclooctanone. Total yield was 3.6% from cyclodecanone.

¹H NMR (270 MHz, CDCl₃) δ9.94 (1H, br.s), 7.60–7.52 (2H, m), 7.40–7.00 (7H, m), 4.35–4.20 (1H, m), 3.20–3.08 (2H, m), 2.40–1.90 (8H, m), 1.80–1.65 (2H, m), 1.65–1.35 (14H, m).

MS m/z (EI direct): 431(M⁺), 354, 332, 304, 217, 118.

This free amine was converted to hydrochloride salt, mp 217° C.

IR(KBr): 3153, 1701 cm⁻¹

Anal. Calcd for $C_{28}H_{37}1N_3O \cdot HCl \cdot 0.5H_2O$: C,70.49; H, 8.24; N, 8.81. Found: C, 70.14; H, 7.99; N, 8.82.

Example 35

1-[1-(1-Phenylcycloundecyl)-4-piperidinyl]-1,3-dihydro-2H-1,3-benzimidazol-2-one This was prepared according to the procedure of Preparation 16, 17, and Example 32 using cycloundecanone instead of cyclooctanone. Total yield was 9.3% from cycloundecanone.

¹H NMR (270 MHz, CDCl₃) δ9.72 (1H, br.s), 7.54–7.49 (2H, m), 7.36–7.00 (7H, m), 4.34–4.20 (1H, m), 3.24–3.10 (2H, m), 2.40–1.85 (8H, m), 1.80–1.65 (4H, m), 1.60–1.25 (14H, m).

MS m/z (EI direct): 445(M⁺), 402, 332, 304, 118, 82.

This free amine was converted to hydrochloride salt, mp 196–202° C.

IR(KBr): 3369, 1697 cm⁻¹

Anal. Calcd for $C_{29}H_{39}1N_3O \cdot HCl \cdot 1.4H_2O$: C,68.66; H, 8.50; N, 8.28. Found: C, 68.67; H, 8.14; N, 8.56.

Example 36

1-[1-(1-Phenylcyclododecyl)-4-piperidinyl]-2H-1,3- benzimidazol-2-one

This was prepared according to the procedure of Preparation 16, 17, and Example 32 using cyclododecanone instead of cyclooctanone. Total yield was 23.4% from cyclododecanone.

¹H NMR (270 MHz, CDCl₃) δ9.79 (1H, br.s), 7.57–7.52 (2H, m), 7.36–7.00 (7H, m), 4.36–4.22 (1H, m), 3.24–3.12 (2H, m), 2.52–2.38 (2H, m), 2.36–2.19 (2H, m), 2.12–1.98 (2H, m), 1.88–1.68 (6H, m), 1.50–1.00 (16H, m).

MS m/z (EI direct): 459(M⁻), 416, 332. 304, 118, 91.

This free amine was convened to hydrochloride salt, mp 251° C.

IR(KBr): 3350, 3148, 1719, 1697 cm⁻¹

Anal. Calcd for $C_{30}H_{41}N_3O \cdot HCl \cdot 0.5CH_3OH \cdot 0.8H_2O$: C,69.57; H, 8.73; N, 7.98. Found: C, 69.61; H, 8.38; N, 8.33.

Example 37

1-{1-[1-(4-Fluorophenyl)cycloheptyl]4-piperidinyl}-1,3-dihydro-2H-1,3-benzimidazol-2-one This was prepared according to the procedure of Example 17 using 4-fluorophenylmagnesium bromide instead of phenylmagnesium bromide. Yield was 89%.

¹H NMR (270 MHz, CDCl₃) δ9.36 (1H, br.s), 7.47 (2H, dd, J=5.4, 8.7 Hz), 7.26–7.18 (1H, m), 7.12–6.94 (5H, m), 4.31–4.18 (1H, m), 3.00–2.84 (2H, m), 2.35–1.97 (8H, m), 1.90–1.40 (10H, m).

MSm/z(EI direct): 407(M⁺), 350, 322, 272, 216, 109, 83.

This free amine was converted to hydrochloride salt, mp 185–192° C.

IR(KBr): 3398, 1705 cm$^{-1}$

Anal. Calcd for $C_{25}H_{30}FN_3O·HCl·0.5H_2O$: C,66.29; H, 7.12; N, 9.28. Found: C, 66.44; H, 7.33; N, 9.01.

Example 38

1-{1-[1-(3-Fluorophenyl)cycloheptyl]-4-piperidinyl}-1,3-dihydro-2H-1,3-benzimidazol-2-one This was prepared according to the procedure of Example 17 using 3-fluorophenylmagnesium bromide instead of phenylmagnesium bromide. Yield was 81%.

$^1$H NMR (270 MHz, CDCl$_3$) δ9.50 (1H, br.s), 7.33–7.21 (4H, m), 7.14–7.00 (3H, m), 6.95–6.87 (1H, m), 4.36–4.18 (1H, m), 3.02–2.86 (2H, m), 2.36–1.95 (8H, m), 1.85–1.40 (10H, m).

MSm/z(EI direct): 407(M$^+$), 350, 312, 272, 216, 109, 82.

This free amine was converted to hydrochloride salt, mp 196–199° C.

IR(KBr): 3400, 1705 cm$^{-1}$

Anal. Calcd for $C_{25}H_{30}FN_3O·HCl·0.3H_2O$: C,66.82; H, 7.09; N, 9.35. Found: C, 66.86; H, 7.23; N, 9.25.

Example 39

1-{1-[1-(4-Methoxyphenyl)cycloheptyl]-4-piperidinyl}-1,3-dihydro-2H-1 3-benzimidazol-2-one This was prepared according to the procedure of Example 17 using 4-methoxyphenylmagnesium bromide instead of phenylmagnesium bromide. Yield was 68%.

$^1$H NMR (270 MHz, CDCl$_3$) δ9.94 (1H, br.s), 7.42 (2H, d, J=8.9 Hz), 7.26–7.20 (1H, m), 7.15–7.02 (3H, m), 6.86 (2H, d, J=8.9 Hz), 4.32–4.16 (1H, m), 3.82 (3H, s), 3.04–2.89 (2H, m), 2.35–1.98 (8H, m), 1.90–1.40 (10H, m).

MS m/z(EI direct): 419(M$^+$), 362, 334, 217, 202, 174, 134, 82.

This free amine was converted to hydrochloride salt, mp 177–187° C.

IR(KBr): 3230, 1699 cm$^{-1}$

Anal. Calcd for $C_{26}H_{33}N_3O_2·HCl·CH_3OH$: C, 66.45; H, 7.85; N, 8.61. Found: C, 66.51; H, 7.79; N, 8.27.

Example 40

1-{1-[1-(3-Methoxyphenyl)cycloheptyl]-4-piperidinyl}-1,3-dihydro-2H-1,3-benzimidazol-2-one This was prepared according to the procedure of Example 17 using 3-methoxyphenylmagnesium bromide instead of phenylmagnesium bromide. Yield was 90%.

$^1$H NMR (270 MHz, CDCl$_3$) δ10.24 (1H, br.s), 7.28–7.20 (2H, m), 7.14–7.00 (5H, m), 6.77 (1H, dd, J=2.1, 8.1 Hz), 4.34–4.18 (1H, m), 3.84 (3H, s), 3.06–2.88 (2.36–2.18 (4H, m), 2.15–1.98 (4H, m), 1.85–1.43 (10H, m).

MS m/z(EI direct): 419(M$^+$), 363, 333, 311, 284, 228, 83.

This free amine was converted to hydrochloride salt, mp 216–218° C.

IR(KBr): 3179, 1697 cm$^{-1}$

Anal. Calcd for $C_{26}H_{33}N_3O_2·HCl·0.25H_2O$: C, 67.81; H, 7.55; N, 9.12. Found: C, 68.16; H, 7.67; N, 8.73.

Example 41

1-{1-[1-(2-Methoxyphenyl)cycloheptyl]-4-piperidinyl}-1,3-dihydro-2H-1,3-benzimidazol-2-one This was prepared according to the procedure of Example 17 using 2-methoxyphenylmagnesium bromide instead of phenylmagnesium bromide. Yield was 90%.

$^1$H NMR (270 MHz, CDCl$_3$) δ9.27 (1H, br.s), 7.40–7.20 (2H, m), 7.10–6.90 (6H, m), 4.40–4.20 (1H, m), 3.91 (3H, s), 3.25–2.90 (2H, m), 2.65–1.35 (18H, m).

MSm/z(EIdirect): 419(M$^+$), 362, 334, 312, 284, 217, 84.

This free amine was converted to hydrochloride salt, mp 167–173° C.

IR(KBr): 3395, 1697 cm$^{-1}$

Anal. Calcd for $C_{26}H_{33}N_3O_2·HCl·1.5H_2O$: C, 64.65; H, 7.72; N, 8.70. Found: C, 64.59; H, 7.72; N, 8.56.

Example 42

1-[1-(4-t-Butyl-1-phenylcyclohexyl)-4-piperidinyl]-1,3-dihydro-2H-1,3-benzimidazol-2-one This was prepared according to the procedure of Preparation 1 and Example 1 using 4-t-butylcyclohexanone instead of cyclohexanone. Total yield was 5%.

$^1$H NMR (270 MHz, CDCl$_3$) δ8.96 (1H, brs), 7.40–7.30 (4H, m), 7.30–7.15 (2H, m), 7.10–7.00 (3H, m), 4.25–4.10 (1H, m), 3.23–3.12 (2H, m), 2.78–2.62 (2H, m), 2.48–2.30 (2H, m), 1.83–1.54 (8H, m), 1.52–1.36 (2H, m), 1.25–1.10 (1H, m), 0.99 (9H, s).

MSm/z(EIdirect): 431(M$^+$), 374, 354, 332, 216, 82.

This free amine was converted to hydrochloride salt, mp 218–219° C.

IR(KBr): 3422, 1697 cm$^{-1}$

Anal. Calcd for $C_{28}H_{37}N_3O·HCl·1.8H_2O$: C. 67.19; H, 8.38; N, 8.40. Found: C, 67.49; H, 8.24; N, 8.05.

Example 43

4-Fluoro-1-[1-(1-phenylcycloheptyl)-4-piperidinyl]-1,3-dihydro-2H-1,3- benzimidazol-2-one This was prepared according to the procedure of Preparation 9 and Example 25 using 2,6-difluoronitrobenzene instead of 5-chloro-2-fluoronitrobenzene. Total yield was 50.9%

$^1$H NMR (270 MHz, CDCl$_3$) δ8.99(1H, br.s), 7.55–7.47 (2H, m), 7.37–7.17 (3H, m), 7.05–6.96 (2H, m), 6.87–6.76 (1H, m), 4.30–4.18 (1H, m), 3.00–2.88 (2H, m), 2.32–2.00 (8H, m), 1.88–1.40 (10H, m).

This free amine was converted to hydrochloride salt, mp 61–64° C.

MSm/z(EIdirect): 407(M), 350, 322, 234, 91.

IR(KBr): 3400, 1709 cm$^{-1}$

Anal. Calcd for $C_{25}H_{30}N_3OF·HCl·1.2H_2O$: C, 64.49; H, 7.23; N, 9.02. Found: C, 64.30; H, 6.98; N, 9.22.

Example 44

5-Fluoro-1-[1-(1-phenylcycloheptyl)-4-piperidinyl]-1,3-dihydro-2H-1,3-benzimidazol-2-one This was prepared according to the procedure of Preparation 9 and Example 25 using 2,5-difluoronitrobenzene instead of 5-chloro-2-fluoronitrobenzene. Total yield was 27.7%.

$^1$H NMR (270 MHz, CDCl$_3$) δ9.45 (1H, br.s), 7.55–7.45 (2H, m), 7.37–7.18 (3H, m), 7.12 (1H, dd, J=4.5, 8.6 Hz), 6.87–6.73 (2H, m), 4.28–4.15 (1H, m), 3.05–2.88 (2H, m), 2.35–2.00 (8H, m), 1.90–1.40 (10H, m).

MS m/z(ESI positive): 408(M+H)$^+$.

This free amine was converted to hydrochloride salt, mp 41–44° C.

IR(KBr): 3400, 1701 cm$^{-1}$

Anal. Calcd for $C_{25}H_{30}N_3OF·HCl·1.4H_2O$: C, 64.00: H, 7.26; N, 8.96. Found: C, 63.81; H, 6.89; N, 8.83.

Example 45

6-Fluoro-1-[1-(1-phenylcycloheptyl)-4-piperidinyl]-1,3-dihydro-2H-1,3-benzimidazol-2-one This was prepared according to the procedure of Preparation 9 and Example 25 using 2,4-difluoronitrobenzene instead of 5-chloro-2-fluoronitrobenzene. Total yield was 49.9%.

¹H NMR (270 MHz, CDCl₃) δ9.41 (1H, br.s), 7.55–7.45 (2H, m), 7.38–7.18 (3H, m), 7.03–6.93 (2H, m), 6.75 (1H, ddd, J=2.0, 8.8, 11.2 Hz), 4.27–4.15 (1H, m), 3.00–2.93 (2H, m), 2.33–2.00 (8H, m), 1.85–1.43 (10H, m).

MS m/z(EI direct): 407(M⁺), 350, 321, 234, 91.

This free amine was converted to hydrochloride salt, mp 51–54° C.

IR(KBr): 3400, 1705 cm⁻¹

Anal. Calcd for $C_{25}H_{30}N_3OF \cdot HCl \cdot 1.1H_2O$: C, 64.74; H, 7.21; N, 9.06. Found: C, 64.51; H, 7.21; N, 9.10.

Example 46
5-Methyl-1-[1-(1-phenylcycloheptyl)-4-piperidinyl]-1,3-dihydro-2H-1,3-benzimidazol-2-one This was prepared according to the procedure of Preparation 9 and Example 25 using 2-fluoro-5-methylnitrobenzene instead of 5-chloro-2-fluoronitrobenzene. Total yield was 47.7%.

¹H NMR (270 MHz, CDCl₃) δ9.13 (1H, br.s), 7.55–7.48 (2H, m), 7.37–7.18 (3H, m), 7.11 (1H, d, J=7.9 Hz), 6.93–6.84 (2H, m), 4.30–4.15 (1H, m), 3.00–2.88 (2H, m), 2.36 (3H, s), 2.36–2.00 (8H, m), 1.85–1.42 (10H, m).

MS m/z(ESI positive): 404(M+H)⁺.

This free amine was converted to hydrochloride salt, mp 45–48° C.

IR(KBr): 3400, 1699 cm⁻¹

Anal. Calcd for $C_{26}H_{33}N_3O \cdot HCl \cdot 1.3H_2O$: C, 67.38; H, 7.96; N, 9.07. Found: C, 67.24; H, 7.60; N, 8.94.

Example 47
6-Methyl-1-[1-(1-phenylcylcloheptyl)-4-piperidinyl]-1,3-dihydro-2H-1,3-benzimidazol-2-one This was prepared according to the procedure of Preparation 9 and Example 25 using 2-fluoro-4-methylnitrobenzene instead of 5-chloro-2-fluoronitrobenzene. Total yield was 60%.

¹H NMR (270 MHz, CDCl₃) δ9.04 (1H, br.s), 7.55–7.48 (2H, m), 7.36–7.18 (3H, m), 7.02 (1H, br.s), 6.94 (1H, d, J=7.9 Hz), 6.84 (1H, br.d, J=7.9 Hz), 4.25–4.10 (1H, m), 3.05–2.90 (2H, m), 2.42 (3H, s), 2.36–2.00 (8H, m), 1.85–1.40 (10H, m).

MS m/z(EI direct): 403(M⁺), 346, 316, 230, 172, 86.

This free amine was converted to hydrochloride salt, mp 151–154° C.

IR(KBr): 3400, 1697 cm⁻¹

Example 48
1-[1-(1-Phenylcycloheptyl)-4-piperidinyl]-5-trifluoromethyl-1,3-dihydro-2H-1,3-benzimidazol-2-one This was prepared according to the procedure of Preparation 9 and Example 25 using 2-fluoro-5-trifluoromethylnitrobenzene instead of 5-chloro-2-fluoronitrobenzene. Total yield was 51.5%.

¹H NMR (270 Hz, CDCl₃) δ10.40 (1H, br.s), 7.55–7.47 (2H, m), 7.40–7.18 (6H, m), 4.35–4.20 (1H, m), 3.05–2.90 (2H, m), 2.35–2.00 (8H, m), 1.90–1.40 (10H, m).

MS m/z(EI direct): 457(M⁺), 400, 372, 285, 172, 91.

This free amine was converted to hydrochloride salt, mp 161–165° C.

IR(KBr): 3400, 1715 cm⁻¹

Anal. Calcd for $C_{26}H_{30}N_3OF_3 \cdot HCl \cdot H_2O$: C, 60.99; H, 6.50; N, 8.21. Found: C, 60.86; H, 6.43; N, 8.75.

Example 49
5-Benzoyl-1-[1-(1-phenylcycloheptyl)-4-piperidinyl]-1,3-dihydro-2H-1,3-benzimidazol-2-one This was prepared according to the procedure of Preparation 9 and Example 25 using 2-fluoro-5-benzoylnitrobenzene instead of 5-chloro-2-fluoronitrobenzene. Total yield was 46.6%.

¹H NMR (270 MHz, CDCl₃) δ9.89 (1H, br.s), 7.80–7.75 (2H, m), 7.65–7.45 (7H, m), 7.40–7.17 (4H, m), 4.36–4.20 (1H, m), 3.05–2.90 (2H, m), 2.40–2.00 (8H, m), 1.90–1.40 (10H, m).

MS m/z(EI direct): 493(M⁺), 436, 408, 320, 238, 91.

This free amine was converted to hydrochloride salt, mp 118–122° C.

IR(KBr): 1715, 1651, 1622 cm⁻¹

Anal. Calcd for $C_{32}H_{35}N_3O_2 \cdot HCl \cdot 0.7H_2O$: C, 70.82; H, 6.95; N, 7.74. Found: C, 70.63; H, 7.03; N, 7.56.

Example 50
7-Chloro-1-[1-(1-phenylcycloheptyl)-4-piperidinyl]-1,3-dihydro-2H-1,3-benzimidazol-2-one This was prepared according to the procedure of Preparation 9 and Example 25 using 2.3-dichloronitrobenzene instead of 5-chloro-2-fluoronitrobenzene. Total yield was 14.9%.

¹H NMR (270 MHz, CDCl₃) δ9.86 (1H, br.s), 7.60–7.48 (2H, m), 7.40–7.15 (3H, m), 7.05–6.90 (3H, m), 4.95–4.77 (1H, m), 3.05–2.85 (2H, m), 2.70–2.53 (2H, m), 2.30–1.95 (6H, m), 1.90–1.40 (10H, m).

MS m/z(EI direct): 423(M⁺), 366, 338, 254. 172, 82.

This free amine was converted to hydrochloride salt, mp 155–158° C.

IR(KBr): 3400, 1701 cm⁻¹

Example 51
5,6-Difluoro-1-[1-(1-phenylcycloheptyl)-4-piperidinyl-1,3-dihydro-2H-1,3-benzimidazol-2-one This was prepared according to the procedure of Preparation 9 and Example 25 using 2,4,5-trifluoronitrobenzene instead of 5-chloro-2-fluoronitrobenzene. Total yield was 14.4%.

¹H NMR (270 MHz, CDCl₃) δ10.09 (1H, br.s), 7.55–7.48 (2H, m), 7.40–7.20 (3H, m), 7.06 (1H, dd, J=6.9, 10.5 Hz), 6.93 (1H, dd, J=6.9, 9.7 Hz), 4.25–4.14 (1H, m), 3.05–2.85 (2H, m), 2.35–2.00 (8H, m), 1.90–1.40 (10H, m).

MS m/z(EI direct): 425(M⁺), 368, 340, 149, 91.

This free amine was converted to hydrochloride salt, mp 173–177° C.

IR(KBr): 3400, 1707 cm⁻¹

Example 52
5,6-Dichloro-1-[1-(1-phenylcycloheptyl)-4-piperidinyl]-1,3-dihydro-2H-1,3-benzimidazol-2-one This was prepared according to the procedure of Preparation 9 and Example 25 using 4,5-dichloro-2-fluoronitrobenzene instead of 5-chloro-2-fluoronitrobenzene. Total yield was 44.2%.

¹H NMR (270 MHz, CDCl₃) δ9.20 (1H, br.s), 7.55–7.48 (2H, m), 7.37–7.19 (4H, m), 7.15 (1H, s), 4.2–34.08 (1H, m), 3.03–2.93 (2H, m), 2.33–2.00 (8H, m), 1.90–1.40 (10H, m).

MS m/z(EI direct): 457(M⁺), 400, 372, 285, 254, 202, 172, 91.

This free amine was converted to hydrochloride salt, mp 130–134° C.

IR(KBr): 1697 cm⁻¹

Anal. Calcd for $C_{25}H_{29}N_3OCl_2 \cdot HCl \cdot 0.4H_2O$: C, 59.80; H, 6.18; N, 8.37. Found: C, 60.03; H, 6.43; N, 7.96.

Example 53
1-[1-(3-Propylspiro[5.5]undecan-3-yl)-4-piperidinyl]-1,3-dihydro-2H-1,3-benzimidazol-2-one This was prepared according to the procedure of Preparation 1 and Example 1 using spiro[5.5]undecan-3-one (Rice, L. M.; Freed, M. E.; Groogan. C. H. *J. Org. Chem.* 1964, 29, 2637–2640) and propylmagnesium bromide instead of phenylmagnesium bromide. Total yield was 63%.

$^1$H NMR (270 MHz, CDCl$_3$) δ9.60 (1H, br.s), 7.27–7.00 (4H, m), 4.41–4.27 (1H, m), 3.17–3.06 (2H, m), 2.40–2.20 (6H, m), 1.85–1.75 (2H, m), 1.75–1.20 (20H, m), 0.93–0.87 (3H, m).

MS m/z(EI): 409(M$^+$), 368, 336, 299, 232, 201, 183, 164, 134, 82.

This free amine was converted to hydrochloride salt, mp 240–247° C.

IR(KBr): 3421, 1697 cm$^{-1}$

Anal. Calcd for C$_{26}$H$_{39}$N$_3$O.HCl.MeOH.0.4H$_2$O: C, 66.82; H, 9.30; N, 8.66. Found: C, 66.98; H, 9.21; N, 8.43.

Example 54

1-[1-(4-Isopropylidene-1-propylcyclohexyl)-4-piperidinyl]-1,3-dihydro-2H-1,3-benzimidazol-2-one This was prepared according to the procedure of Preparation 1 and Example 1 using 4-isopropylidenecyclohexanone (Lambert, J. B.; Ciro. S. M. *J. Org. Chem.* 1996, 61 1940) and propylmagnesium bromide instead of phenylmagnesium bromide. Total yield was 13.5%.

$^1$H NMR (270 MHz, CDCl$_3$) δ9.47 (1H, br.s), 7.26–7.00 (4H, m), 4.42–4.26 (1H, m), 3.22–3.08 (2H, m), 2.45–2.22 (8H, m), 1.95–1.75 (4H, m), 1.70 (6H, s), 1.45–1.20 (6H, m), 0.90 (3H, br.t, J=6.9 Hz).

MS m/z(EI): 381(M$^+$), 339,218, 164, 121, 82.

This free amine was converted to hydrochloride salt. mp 252° C.

IR(KBr): 33404, 1699 cm$^{-1}$

Anal. Calcd for C$_{24}$H$_{35}$N$_3$O.HCl.2H$_2$O.0.2CH$_2$Cl$_2$: C, 61.71; H, 8.64; N, 8.92. Found: C, 61.71; H, 8.32; N, 8.66.

Example 55

1-[1-(1-Methylcyclononyl)-4-piperidinyl]-1,3-dihydro-2H-1,3-benzimidazol-2-one

This was prepared according to the procedure of Preparation 1 and Example 1 using cyclononanone and methylmagnesium bromide instead of cyclohexanone and phenylmagnesium bromide. Total yield was 27.3%.

$^1$H NMR (270 MHz, CDCl$_3$) δ9.32 (1H, br.s), 7.33–7.03 (4H, m), 4.38–4.28 (1H, m), 3.22–3.10 (2H, m), 2.44–2.18 (4H, m), 1.90–1.36 (18H, m), 0.83 (3H, s).

MS m/z(EI): 355(M$^+$), 339, 312, 271, 217, 136, 122, 83.

This free amine was converted to hydrochloride salt to give amorphous solid.

IR(KBr): 3369, 1693 cm$^{-1}$

Anal. Calcd for C$_{22}$H$_{33}$N$_3$O.HCl.MeOH.0.15CH$_2$Cl$_2$: C, 63.66; H, 8.84; N, 9.62. Found: C, 63.66; H, 8.572; N, 9.69.

Example 56

1-[1-(1-Ethylcyclononyl)-4-piperidinyl]-1,3-dihydro-2H-1,3-benzimidazol-2-one

This was prepared according to the procedure of Preparation 1 and Example 1 using cyclononanone and ethylmagnesium bromide instead of cyclohexanone and phenylmagnesium bromide. Total yield was 22.4%.

$^1$H NMR (270 MHz, CDCl$_3$) δ9.19 (1H, br.s), 7.29–7.00 (4H, m), 4.36–4.26 (1H, m), 3.24–3.14 (2H, m), 2.46–2.18 (4H, m), 1.83–1.20 (20H, m), 0.85 (3H, t, J=7.4 Hz).

MS m/z(EI): 369(M$^+$), 341, 284. 82.

This free amine was converted to hydrochloride salt to give amorphous solid.

IR(KBr): 3400, 1686 cm$^{-1}$

Anal. Calcd for C$_{23}$H$_{35}$N$_3$O.HCl.H$_2$O.0.5CH$_2$Cl$_2$: C, 59.99; H, 8.54; N, 9.13. Found: C, 59.62; H, 8.39; N, 9.22.

Example 57

1-[1-(1-Methylcyclooctyl)-4-piperidinyl]-1,3-dihydro-2H-1,3-benzimidazol-2-one

This was prepared according to the procedure of Preparation 1 and Example 1 using cyclooctanone and methylmagnesium bromide instead of cyclohexanone and phenylmagnesium bromide. Total yield was 51.8%.

$^1$H NMR (270 MHz, CDCl$_3$) δ9.95 (1H, br.s), 7.32–7.03 (4H, m), 4.42–4.26 (1H, m), 3.18–3.05 (2H, m), 2.45–2.18 (4H, m), 1.94–1.28 (16H, m), 0.87 (3H, s).

MS m/z(EI): 341(M$^+$), 325, 270, 217, 136, 83.

This free amine was converted to hydrochloride salt to give amorphous solid.

IR(KBr): 3400, 1692 cm$^{-1}$

Anal. Calcd for C$_{21}$H$_{31}$N$_3$O.HCl.0.4H$_2$O: C, 65.49; H, 8.58; N, 10.91. Found: C, 65.49; H, 8.64; N, 10.94.

Example 58

1-[1-(1-Ethylcyclooctyl)-4-piperidinyl]-1,3-dihydro-2H-1,3-benzimidazol-2-one

This was prepared according to the procedure of Preparation 1and Example 1using cyclooctanone and ethylmagnesium bromide instead of cyclohexanone and phenylmagnesium bromide. Total yield was 34.8%.

$^1$H NMR (270 MHz, CDCl$_3$) δ9.49 (1H, br.s), 7.29–7.00 (4H, m), 4.39–4.25 (1H, m), 3.14–3.02 (2H, m), 2.41–2.22 (4H, m), 1.85–1.30 (18H, m), 0.86 (3H, t, J=7.4 Hz).

MS m/z(EI): 381(M$^+$), 339, 218. 164, 121, 82.

This free amine was converted to hydrochloride salt to give amorphous solid.

IR(KBr): 3400, 1686 cm$^{-1}$

Anal. Calcd for C$_{22}$H$_{33}$N$_3$O.HCl.0.5H$_2$O.0.5CH$_2$Cl$_2$: C, 60.94; H, 8.18; N, 9.48. Found: C, 60.74; H, 8.28; N, 9.35.

Example 59

1-[4-Piperidinyl-1-(1-propylcyclooctyl)]-1,3-dihydro-2H-1,3-benzimidazol-2-one

This was prepared according to the procedure of Preparation 1 and Example 1using cyclooctanone and propylmagnesium bromide instead of cyclohexanone and phenylmagnesium bromide. Total yield was 26.3%.

$^1$H NMR (270 MHz, CDCl$_3$) δ10.05 (1H, br.s), 7.26–7.00 (4H, m), 4.40–4.20 (1H, m), 3.15–3.00 (2H, m), 2.42–2.15 (4H, m), 1.95–1.20 (20H, m), 0.95–0.80 (3H, m).

MS m/z(EI): 381(M$^+$), 369, 327,298, 257, 217, 134, 82.

This free amine was converted to hydrochloride salt to give amorphous solid.

IR(KBr): 3400, 1686 cm$^{-1}$

Anal. Calcd for C$_{23}$H$_{35}$N$_3$O.HCl.MeOH.0.6CH$_2$Cl$_2$: C, 60.42; H, 8.49; N, 8.59. Found: C, 60.44; H, 8.34; N, 8.28.

Example 60

1-[1-(1-Phenylcyclohept-4-enyl)-4-Piperidinyl]1,3-dihydro-2H-1,3-benzimidazol-2-one This was prepared according to the procedure of Preparation 1 and Example 1using 4-cycloheptenone ( J. A. Marshall et al., *J. Org. Chem.,* 1982, 47, 693–698) instead of cyclohexanone. Total yield was 25.6%.

$^1$H NMR (270 MHz, CDCl$_3$+DMSOd$_6$) δ10.57 (1H, br.s), 7.45–6.93 (9H, m), 5.73–5.68 (2H, m), 4.07–4.00 (1H, m), 3.22–3.12 (2H, m), 2.50–1.62 (14H, m).

MS m/z(EI): 387(M$^+$), 310, 254, 216, 185, 83.

This free amine was converted to hydrochloride salt to give amorphous solid.

IR(KBr): 3252, 1705 cm$^{-1}$

Anal. Calcd for $C_{25}H_{29}N_3O \cdot HCl \cdot MeOH \cdot 0.5H_2O$: C, 67.15; H, 7.59; N, 9.04. Found: C, 66.94; H, 7.48; N, 8.80.

Example 61
1-[1-(1-Methylcyclohept-4-enyl)-4-Piperidinyl]-1,3-dihydro-2H-1,3-benzimidazol -2-one This was prepared according to the procedure of Preparation 1and Example 1using 4-cycloheptenone ( J. A. Marshall et al., *J. Org. Chem.*, 1982, 47, 693–698) instead of cyclohexanone and methylmagnesium bromide instead of phenylmagnesium bromide. Total yield was 49.6%.

$^1$H NMR (270 MHz, CDCl$_3$+DMSOd$_6$) δ10.57 (1H, br.s), 7.45–6.93 (9H, m), 5.73–5.68 (2H, m), 4.07–4.00 (1H, m), 3.22–3.12 (2H, m), 2.50–1.62 (14H, m).

MS m/z(EI): 387(M$^+$), 310, 254. 216, 185, 83.

This free amine was converted to hydrochloride salt to give amorphous solid.

IR(KBr): 1692 cm$^{-1}$

Anal. Calcd for $C_{20}H_{27}N_3O \cdot HCl \cdot MeOH$: C, 64.03; H, 8.19; N, 10.67. Found: C, 64.05; H, 7.98; N, 10.62.

Example 62
1-[1-(1-Ethylcyclohept-4-enyl)-4-Piperidinyl]-1,3-dihydro-2H-1,3-benzimidazol-2-one This was prepared according to the procedure of Example 61 using ethylmagnesium bromide instead of methylmagnesium bromide. Total yield was 54%.

$^1$H NMR (270 MHz, CDCl$_3$) δ9.98 (1H, br.s), 7.28–7.17 (1H, m), 7.09–6.98 (3H, m), 5.80–5.72 (2H, m), 4.37–4.25 (1H, m), 3.17–3.05 (2H, m), 2.56–2.28 (7H, m), 2.05–1.74 (5H, m), 1.64–1.44 (4H, m), 0.86 (3H, t, J=7.4 Hz).

MS m/z(EI): 339(M$^+$), 312, 272, 206, 176, 137, 82.

This free amine was convened to hydrochloride salt to give amorphous solid.

IR(KBr): 3377, 1703 cm$^{-1}$

Anal. Calcd for $C_{21}H_{29}N_3O \cdot HCl \cdot 1.55H_2O$: C, 62.45; H, 8.26; N, 10.40. Found: C, 62.71; H, 8.21; N, 10.00.

Example 63
1-[1-(1-Propylcyclohept-4-enyl)-4-Piperidinyl]-1,3-dihydro-2H-1,3-benzimidazol -2-one This was prepared according to the procedure of Example 61 using propylmagnesium bromide instead of methylmagnesium bromide. Total yield was 35%.

$^1$H NMR (270 MHz, CDCl$_3$) δ10.39 (1H, s), 7.30–7.20 (1H, m), 7.18–7.00 (3H, m), 5.82–5.70 (2H, m), 4.44–4.26 (1H, m), 3.16–3.02 (2H, m), 2.48–2.24 (6H, m), 2.05–1.75 (6H, m), 1.62–1.20 (6H, m), 0.91 (3H, t, J=6.9 Hz).

MS m/z(EI): 353(M$^+$), 311, 220, 1765, 82.

This free amine was converted to hydrochloride salt to give amorphous solid.

IR(KBr): 3400, 1690 cm$^{-1}$

Anal. Calcd for $C_{22}H_{31}N_3O \cdot HCl \cdot 2.3H_2O$: C, 61.25; H, 8.55; N, 9.74. Found: C, 61.21; H, 8.21; N, 9.40.

Preparation 18
t-Butyl N-(2-{2-Oxo-3-[1-(1-phenylcycloheptyl)-4-piperidinyl]2,3-dihydro-1H-benzimidazol-1-yl}ethyl)carbamate To a stirred mixture of 1-[1-(1-phenylcycloheptyl)-4-piperidyl]-1,3-dihydro-2H-1,3-benzimidazol-2-one (100 mg, 0.257 mmol, this was prepared as Example 17) and THF (2 ml) was added t-BuOK (35 mg, 0.308 mmol) at 0° C. Then N-(t-butoxycarbonyl)-2-bromoethylamine (86 mg. 0.385 mmol, this was reported by E. Vedejs et al. *J. Org. Chem.* 1988, 33, 2226–2232). NaI (8 mg, 0.0513 mmol), and DMF (0.5 ml) were added to the reaction mixture. After 8 h stirring at 60° C., the reaction mixture was concentrated in vacuo. The residue was diluted with CH$_2$Cl$_2$. washed with water, dried (Na$_2$SO$_4$). and filtered. The filtrate was concentrated and the residue was purified by preparative TLC (MeOH/CH$_2$Cl$_2$: 1/10) to give 98 mg (71.6%) of amorphous solid.

$^1$H NMR (270 MHz, CDCl$_3$) δ7.54–7.43 (2H, m), 7.36–7.14 (4H, mz), 7.10–6.97 (3H, m), 4.95–4.85 (1H, m), 4.26–4.17 (1H, m), 4.03–3.90 (2H, m), 3.49–3.37 (2H, m), 2.98–2.85 (2H, m), 2.30–2.16 (4H, m), 2.12–1.98 (4H, m), 1.85–1.35 (10H, m), 1.41 (9s).

Example 64
1-(2-Aminoethyl)-3-[1-(1-phenylcycloheptyl)-4-piperidinyl]-1,3-dihydro-2H -benzimidazol-2-one dihydrochloride A mixture of t-butyl N-(2-{2-oxo-3-[1-(1-phenylcycloheptyl)-4-piperidyl]-2,3-dihydro-1H-benzimidazol-1-yl}ethyl)carbamate (35 mg, 0.0657 mmol, this was prepared as Preparation 18) and HCl solution in MeOH (2 ml) was stirred at room temperature for 15 h. The reaction mixture was concentrated in vacuo to give 33.2 mg (100%) of white solid.

$^1$H NMR (270 MHz, DMSOd$_6$) δ10.60 (1H, br.s), 8.20 (3H, br.s), 8.01 (1H, br.d, J=7.1 Hz). 7.94–7.84 (2H, m), 7.56–7.45 (3H, m), 7.37–7.27 (1H, m), 7.13–6.99 (2H, m), 4.63–4.538 (1H, m), 4.15–4.01 (2H, m), 3.50–3.30 (4H, m), 3.20–2.97 (6H, m), 2.80–2.68 (2H, m), 1.90–1.75 (4H, m), 1.70–1.20 (6H, m).

MS m/z (EI direct): 432(M$^+$), 375, 355, 255, 178.

IR(KBr): 3391, 1690 cm$^{-1}$

Anal. Calcd for $C_{27}H_{36}N_4O \cdot 2HCl \cdot 2.5H_2$: C, 58.90; H, 7.87; N, 10.18. Found: C, 58.82; H, 7.73; N, 9.92.

Example 65
N-(2-{2-Oxo-3-1-(1-phenylcycloheptyl)-4-piperidinyl]-2,3-dihydro-1H-benzimidazol-1-yl}ethyl)guanidine dihydrochloride A mixture of t-butyl N-(2-{2-oxo-3-[1-(1-phenylcycloheptyl)-4-piperidyl]-2,3-dihydro -1H-benzimidazol-1-yl}ethyl)carbamate (58.9 mg, 0.111 mmol) and HCl solution in MeOH (2 ml) was stirred at room temperature for 4 h. After evaporation of the solvent, the residue was dissolved in DMF (2 ml). To stirred mixture was added triethylamine (37 μl, 0.265 mmol) and N, N'-bis Boc guanylpyrazole (41 mg, 0.133 mmol, this was prepared according to the following reported procedure: M. S. Bernatowicz, et al., *Tetrahedron Lett.*, 1993, 34, 3389–3392) at room temperature. After 2 h stirring, the solvent was evaporated. The residue was dissolved in CH$_2$Cl$_2$, washed with brine, dried (Na$_2$SO$_4$). filtered, and concentrated. The residue was purified by preparative TLC (hexane/ethyl acetate:3/1) to give 47.1 mg (63.1%) of amorphous solid. A mixture of this amorphous solid (47.1 mg, 0.0698 mmol), trifluoroacetic acid (0.5 ml), and CH$_2$Cl$_2$ (1ml) was stirred at room temperature for 4 h. After evaporation of the solvent, the residue was dissolved in HCl solution in MeOH (2 ml). Then the solvent was evaporated in vacuo to give 38.2 mg (100%) of amorphous solid.

$^1$H NMR (270 MHz, DMSOd$_6$) δ7.95–7.80 (4H, m), 7.70–7.40 (5H, m), 7.30–7.00 (6H, m), 4.67–4.50 (1H, m), 4.00–3.90 (2H, m). 3.25–2.85 (8H, m), 2.85–2.68 (4H, m), 1.95–1.75 (4H, m), 1.65–1.20 (6H, m).

MS(ESI positive) m/z: 475(M+H)$^+$.

IR(KBr): 3350, 3167, 1670, 1616 cm$^{-1}$

Anal. Calcd for $C_{28}H_{38}N_6O \cdot 2HCl \cdot 2H_2O$: C, 57.63; H, 7.60; N, 14.40. Found: C, 57.94; H, 7.83; N, 14.30.

Example 66
1-[2-(Methylamino)ethyl]-3-[1-(1-phenylcycloheptyl)-4-piperidinyl]-1,3-dihydro-2H-benzimidazol-2-one To a stirred solution of t-butyl N-(2-{2-oxo-3-[1-(1-phenylcycloheptyl)-4-piperidyl]-2,3-dihydro-1H-benzimidazol-1-yl}ethyl)carbamate (50 mg, 0.939 mmol) in THF (1 ml) was added NaH (6 mg, 0.141 mmol) followed by addition of MeI (7 µl, 0.113 mmol) at 0° C. and the resulting mixture was stirred at room temperature for 15 h. The reaction mixture was poured into saturated NaHCO$_3$ solution and extracted with CH$_2$Cl$_2$. The extracts combined were dried (Na$_2$SO$_4$), filtered, and concentrated. The residue was purified by preparative TLC (acetone/hexane:1/2) to give 44.8 mg (87.3%) of amorphous solid. A mixture of this solid (44.7 mg, 0.0818 mmol) and HCl solution in MeOH (2 ml) was stirred at room temperature for 4 h. Evaporation of the solvent gave 42.5 mg (100%) of amorphous solid.

$^1$H NMR (270 MHz, CDCl$_3$) δ8.00–7.75 (4H, m), 7.55–7.25 (5H, m), 7.15–7.00 (3H, m), 4.65–4.50 (1H, m), 4.20–4.08 (2H, m), 3.25–2.55 (15H, m), 1.95–1.75 (4H, m), 1.65–1.20 (6H, m).

MS(ESI positive) m/z: 447(M+H)$^+$.

This free amine was converted to hydrochloride salt, mp 217° C.

IR(KBr): 3402, 1670 cm$^{-1}$

Anal. Calcd for C$_{28}$H$_{38}$N$_4$O.2HCl.1.6H$_2$O: C, 61.93; H, 8.10; N, 9.96. Found: C, 62.04; H, 8.41; N, 9.79.

Example 67
N-(2-{2-Oxo-3-1-(1-phenylcycloheptyl)-4-piperidinyl]-2,3-dihydro-1H -benzimidazol-1-yl}ethyl)acetamide A mixture of t-butyl N-(2-{2-oxo-3-[1-(1-phenylcycloheptyl)-4-piperidyl]-2,3-dihydro-1H-benzimidazol-1-yl}ethyl)carbamate (50 mg. 0.0939 mmol) and HCl solution in MeOH (2 ml) was stirred at room temperature for 4 h. After evaporation of the solvent, the residue was dissolved in CH$_2$Cl$_2$ (1 ml). To this solution was added triethylamine (52 µl, 0.375 mmol) and acetyl chloride (13 µl, 0.188 mmol) at room temperature.

After 12 h stirring, the reaction mixture was diluted with CH$_2$Cl$_2$, washed with water, dried (NA$_2$SO$_4$), filtered, and concentrated. The residue was purified by preparative TLC (MeOH/CH$_2$Cl$_2$:1/10) to give 16.8 mg (37.8%) of white solid.

$^1$H NMR (270 MHz, CDCl$_3$) δ7.51 (1H, br.d, J=7.4 Hz), 7.38–7.00 (8H, m), 6.47–6.35 (1H, m), 4.30–4.14 (1H, m), 4.02 (2H, t, J=5.4 Hz), 3.57 (2H, dt, J=5.4, 5.9 Hz), 3.04–2.86 (2H, m), 2.40–2.20 (4H, m), 2.20–2.00 (4H, m), 1.94 (3H, s), 1.90–1.40 (10H, m).

MS m/z (EI direct): 474(M$^+$), 418, 398, 301, 255, 220, 198, 82.

This free amine was converted to hydrochloride salt.

IR(KBr): 3350,1684 cm$^{-1}$

Anal. Calcd for C$_{29}$H$_{38}$N$_4$O$_2$.HCl2.5H$_2$O: C, 62.63; H, 7.97; N, 10.07. Found: C, 62.48; H, 8.29; N, 9.98.

Example 68
(2R)-N-(2-{2-Oxo-3-[1-(1-phenylcycloheptyl)-4-piperidinyl]-2,3-dihydro-1H -benzimidazol-1-yl}ethyl) tetrahydro-1H-pyrrole-2-carboxamide dihydrochloride A mixture of t-butyl N-(2-{2-oxo-3-[1-(1-phenylcycloheptyl)-4-piperidyl]-2,3-dihydro-1H-benzimidazol-1-yl}ethyl)carbamate (50 mg, 0.0939 mmol) and HCl solution in MeOH (2 ml) was stirred at room temperature for 4 h. After evaporation of the solvent, the residue was dissolved in DMF (1 ml). To this stirred solution was added N-(t-butoxycarbonyl)-L-proline (40 mg, 0.188 mmol), WSCD-HCl (36 mg, 0.188 mmol), -1-hydroxybenzotriazole (25 mg, 0.188 mmol), and triethylamine (52 µl, 0.375 mmol) at room temperature. After 12 h stirring, the reaction mixture was diluted with CH$_2$Cl$_2$, washed with water, dried (Na$_2$SO$_4$), filtered, and concentrated. The residue was purified by preparative TLC (MeOH/CH$_2$Cl$_2$:1/10) to give 34.4 mg (58.2%) of colorless oil. A mixture of this solid (34.4 mg, 0.0546 mmol) and HCl solution in MeOH (3 ml) was stirred at room temperature for 4 h. Evaporation of the solvent gave 32.9 mg (100%) of white amorphous solid.

$^1$H NMR (270 MHz, DMSOd$_6$) δ8.80–8.65 (1H, m), 8.55–8.35 (1H, m), 8.00–7.75 (3H, m), 7.60–7.40 (3H, m), 7.22–7.00 (3H, m), 4.70–4.50 (1H, m), 4.10–3.85 (4H, m), 3.30–2.40 (15H, m), 2.15–2.00 (1H, m), 1.95–1.20 (13H, m).

MS m/z (EI direct): 529(M$^+$), 472, 403, 356, 275.

This free amine was converted to hydrochloride salt.

IR(KBr): 3402, 3236. 1684 cm$^{-1}$

Anal. Calcd for C$_{32}$H$_{43}$N$_5$O$_2$.2HCl.0.5H$_2$O: C, 59.68; H, 7.24; N, 10.71. Found: C, 59.49; H, 7.14; N, 10.67.

Example 69
N-(2-{2-Oxo-3[-1-(1-phenylcycloheptyl)-4-piperidinyl]-2,3-dihydro-1H -benzimidazol-1-yl}ethyl)nicotinamide dihydrochloride A mixture of t-butyl N-(2-{2-oxo-3-[1-(1-phenylcycloheptyl)-4-piperidyl]-2,3-dihydro-1H-benzimidazol-1-yl}ethyl)carbamate (50 mg, 0.0939 mmol) and HCl solution in MeOH (2 ml) was stirred at room temperature for 4 h. After evaporation of the solvent, the residue was dissolved in pyridine (1 ml). To this solution was added nicotynoyl chloride hydrochloride (19 mg, 0.113 mmol) at room temperature. After 15 h stirring, the reaction mixture was diluted with CH$_2$Cl$_2$, washed with water, dried (Na$_2$SO$_4$), filtered, and concentrated. The residue was purified by preparative TLC (MeOH/CH$_2$Cl$_2$:1/10) to give 22.5 mg (44.6%) of colorless oil.

$^1$H NMR (270 MHz, CDCl$_3$) δ9.03 (1H, br.d, J=2.2 Hz), 8.70 (1H, dd, J=1.6, 4.8 Hz), 8.13 (1H, ddd, J=1.6, 2.3, 7.9 Hz), 7.51 (1H, br.d, J=7.4 Hz), 7.86–7.77 (1H, m), 7.54–7.48 (2H, m), 7.39–7.18 (4H, m), 7.13–7.03 (3H, m), 4.30–4.14 (1H, m), 4.17 (2H, t, J=5.8 Hz), 3.85–3.75 (2H, m), 3.00–2.90 (2H, m), 2.35–2.18 (4H, m), 2.18–2.00 (4H, m), 1.86–1.40 (10H, m).

MS m/z (EI direct): 537(M$^+$), 480, 364, 255, 214, 82.

This free amine was converted to hydrochloride salt.

IR(KBr): 3400, 3238, 1684 cm$^{-1}$

Anal. Calcd for C$_{33}$H$_{39}$N$_5$O$_2$.2HCl.2H$_2$O: C, 61.29; H, 7.01; N, 10.83. Found: C, 61.54; H, 7.36; N, 10.83.

Example 70
1-(3-Aminopropyl)-3-[1-(1-phenylcycloheptyl)-4-piperidinyl]-1,3-dihydro-2H-benzimidazol-2-one dihydrochloride This was prepared according to the procedure of Preparation 18 and Example 64 using N-(t-butoxycarbonyl)-3-bromopropylamine (this was reported by B. H. Lee et al. *J. Org. Chem.* 1983, 48 24–31) instead of N-(t-butoxycarbonyl)-2-bromoethylamine. Yield was 85.9%.

$^1$H NMR (270 MHz, DMSOd$_6$) δ8.10–7.65 (6H, m), 7.55–7.40 (3H, m), 7.30–7.20 (1H, m), 7.15–6.95 (2H, m), 4.65–4.50 (1H, m), 3.95–3.80 (2H, m), 3.50–2.60 (7H, m), 2.00–1.20 (18H, m).

MS(ESI positive) m/z: 447(M+H)$^+$.

IR(KBr): 3412, 1684 cm$^{-1}$

Anal. Calcd for C$^{28}$H$^{38}$N$^4$O.2HCl.2H$_2$O: C, 60.53; H, 7.98; N, 10.08. Found: C, 60.86; H, 8.34; N, 10.26.

Example 71
1-(6-Aminohexyl)-3-[1-(1-phenylcycloheptyl)-4-piperidinyl]-1,3-dihydro-2H-benzimidazol-2-one dihydrochloride This was prepared according to the procedure of Preparation 18 and Example 64 using N-(t-butoxycarbonyl)-6-methanesulfonyloxyhexylamine (this was reported by H. F. Voss et al. DE 3003959) instead of N-(t-butoxycarbonyl)-2-bromoethylamine. Yield was 60.9%.

$^1$H NMR (270 MHz, DMSOd$_6$) δ8.00–7.65 (6H, m), 7.60–7.40 (3H, m), 7.20–7.15 (1H, m), 7.15–6.95 (2H, m), 4.65–4.50 (1H, m), 3.85–3.75 (2H, m), 3.25–2.40 (7H, m), 1.90–1.20 (24H, m).

MS(ESI positive) m/z: 489(M+H)$^+$.
IR(KBr): 3400, 1686 cm$^{-1}$
Anal. Calcd for C$_{31}$H$_{44}$N$_4$O.2HCl.1.6H$_2$O: C, 63.06; H, 8.40; N, 9.49. Found: C, 63.43; H, 8.81; N, 9.47.

Example 72
1-[1-(1-Phenylcycloheptyl)-4-piperidinyl]-3-(2-piperidinoethyl-1,3-dihydro-2H-benzimidazol-2-one This was prepared according to the procedure of Preparation 18 using 1-(2-chloroethyl)piperidine hydrochloride instead of N-(t-butoxycarbonyl)-2-bromoethylamine. Yield was 24.3%.

$^1$H NMR (270 MHz, CDCl$_3$) δ7.54–7.46 (2H, m), 7.36–6.98 (7H, m), 4.29–4.12 (1H, m), 4.00 (2H, dd, J=7.4, 7.7 Hz), 3.00–2.86 (2H, m), 2.63 (2H, dd, J=7.4, 7.7 Hz), 2.54 –2.45 (4H, m), 2.32–2.18 (4H, m), 2.12–1.90 (4H, m), 1.84–1.38 (16H, m).

MS m/z(EI direct): 500(M$^+$), 443, 422, 389, 327, 246, 91.
This free amine was converted to hydrochloride salt.
IR(KBr): 3369, 1686 cm$^{-1}$
Anal. Calcd for C$_{32}$H$_{44}$N$_4$O.5HCl.2.5H$_2$O: C, 62.12; H, 8.31; N, 9.06. Found: C, 62.36; H, 8.59; N, 8.95.

Example 73
1-(2-morpholinoethyl)-3-[1-(1-Phenylcycloheptyl)-4-piperidinyl]-1,3-dihydro-2H-benzimidazol-2-one This was prepared according to the procedure of Preparation 18 using 1-(2-chloroethyl)morpholine hydrochloride instead of N-(t-butoxycarbonyl)-2-bromoethylamine. Yield was 46.9%.

$^1$H NMR (270 MHz, CDCl$_3$) δ7.55–7.47 (2H, m), 7.36–7.28 (2H, m), 7.25–7.17 (2H, m), 7.12–6.96 (3H, m), 4.28–4.10 (1H, m), 3.99 (2H, dd, J=6.9, 7.4 Hz), 3.72–3.65 (4H, m), 3.00–2.88 (2H, m), 2.66 (2H, dd, J=6.9, 7.2 Hz), 2.58–2.50 (4H, m), 2.36–2.16 (4H, m), 2.14–2.00 (4H, m), 1.84–1.40 (10H, m).

MS m/z(EI direct): 502(M$^+$), 445, 424, 389, 329, 248, 100.
This free amine was converted to hydrochloride salt.
IR(KBr): 3404, 1686 cm$^{-1}$
Anal. Calcd for C$_{31}$H$_{42}$N$_4$O$_2$.2HCl.2.5H$_2$O: C. 59.99; H, 7.96; N, 9.03. Found: C, 60.29; H, 8.05; N, 8.87.

Example 74
1-[2-(Dimethylamino)ethyl]-3-[1-(1-Phenylcycloheptyl)-4-piperidinyl]-1,3-dihydro-2H-benzimidazol-2-one This was prepared according to the procedure of Preparation 18 using 2-dimethylaminoethyl chloride hydrochloride instead of N-(t-butoxycarbonyl)-2-bromoethylamine. Yield was 24.8%.

$^1$H NMR (270 MHz, CDCl$_3$) δ7.57–7.48 (2H, m), 7.38–7.28 (2H, m), 7.26–7.17 (2H m), 7.12–6.98 (3H, m), 4.30–4.17 (1H, m), 3.97 (2H, dd, J=6.9, 7.9 Hz), 3.03–2.90 (2H, m), 2.63 (2H, dd, J=7.2, 7.4 Hz), 2.32 (6H, s). 2.32–2.00 (4H, m), 1.90–1.40 (10H, m).

MS m/z(EI direct): 460(M$^+$), 403, 389, 332, 287, 206.
This free amine was converted to hydrochloride salt.
IR(KBr): 3385, 1697 cm$^{-1}$
Anal. Calcd for C$_{29}$H$_{40}$N$_4$O.2HCl.2.5H$_2$O: C, 60.20; H, 8.19; N, 9.68. Found: C, 60.34; H, 8.56; N, 9.59.

Example 75
1-[2-(Diisopropylamino)ethyl]-3-[1-(1-Phenylcycloheptyl)-4-piperidinyl]-1,3-dihydro-2H-benzimidazol-2-one This was prepared according to the procedure of Preparation 18 using 2-diisopropylaminoethyl chloride hydrochloride instead of N-(t-butoxycarbonyl)-2-bromoethylamine. Yield was 32.5%.

$^1$H NMR (270 MHz, CDCl$_3$) δ7.55–7.47 (2H, m), 7.36–7.28 (2H, m), 7.24–7.16 (2H, m), 7.10–6.94 (3H, m), 4.30–4.15 (1H, m), 3.87–3.74 (2H, m), 3.10–2.86 (4H, m), 2.76–2.65 (2H, m), 2.32–2.16 (4H, m), 2.12–1.94 (4H, m), 1.84–1.40 (10H, m), 1.00 (12H, d, J=6.2 Hz).

MS(ESI positive) m/z: 517(M+H)$^+$.
This free amine was converted to hydrochloride salt.
IR(KBr): 3402, 1690 cm$^{-1}$
Anal. Calcd for C$_{33}$H$_{48}$N$_4$O.2HCl.2.4H$_2$O: C, 62.62; H. 8.73; N, 8.85. Found: C, 62.94; H, 9.09; N, 8.78.

Example 76
1-[1-(1-Phenylcycloheptyl)-4-piperidinyl]-3-[2-(4-piperidinyl)ethyl-]-1,3-dihydro-2H-benzimidazol-2-one dihydrochloride This was prepared according to the procedure of Preparation 18 and Example 64 using N-(t-butoxycarbonyl)-4-(2-methanesufonyloxyethyl)piperidine (this was reported by Edmonds-Alt et al. FR 2676226) instead of N-(t-butoxycarbonyl)-2-bromoethylamine. Yield was 36.3%.

$^1$H NMR (270 MHz, DMSOd$_6$) δ10.35–10.20 (1H, m), 8.95–8.80 (1H, m), 8.70–8.55 (1H, m), 7.95–7.80 (3H, m), 7.60–7.40 (3H, m), 7.25–7.15 (1H, m), 7.15–7.00 (2H, m), 4.65–4.50 (1H, m), 3.90–3.80 (2H, m), 3.30–2.40 (11H, m), 2.00–1.20 (20H, m),

MS(ESI positive) m/z: 501(M+H)$^+$.
IR(KBr): 3385, 1684 cm$^{-1}$
Anal. Calcd for C$_{32}$H$_{44}$N$_4$O.2HCl2.5H$_2$O: C, 62.12; H, 8.31; N, 9.06. Found: C, 62.35; H, 8.68; N, 9.04.

Example 77
1-[1-(1-Phenylcycloheptyl)-4-piperidinyl]-3-[2-(1H-pyrrol-1-yl)ethyl]-1,3-dihydro-2H-benzimidazol-2-one This was prepared according to the procedure of Preparation 18 using 2-bromoethylpyrrole instead of N-(t-butoxycarbonyl)-2-bromoethylamine. Total yield was52.5%.

$^1$H NMR (270 MHz, CDCl$_3$) δ7.55–7.45 (2H, m), 7.38–7.28 (2H, m), 7.25–7.17 (2H, m), 7.10–6.93 (3H, m), 6.56 (2H, dd, J=2.0, 2.1 Hz), 6.08 (2H, dd, J=2.0, 2.1 Hz), 4.24 –4.06 (5H, m), 2.99–2.90 (2H, m), 2.33–2.20 (4H, m), 2.14–2.03 (4H, m), 1.82–1.42 (10H, m).

MS(ESI positive) m/z: 483(M+H)$^+$.
This free amine was converted to hydrochloride salt.
IR(KBr): 3396, 1684 cm$^{-1}$
Anal. Calcd for C$_{31}$H$_{38}$N$_4$O.HCl.1H$_2$O: C, 69.32; H, 7.69; N, 10.43. Found: C, 69.14; H, 7.95; N, 10.41.

Example 78
1-[1-(1-Phenylcycloheptyl)-4-piperidinyl]-3-(2-piperazinoethyl)-1,3-dihydro-2H-benzimidazol-2-one This was prepared according to the procedure of Preparation 18 and Example 64 using N-(t-butoxycarbonyl)-4-(2-methanesufonyloxyethyl)piperazine (this was reported by J. M. McCall et al. WO 8701706) instead of N-(t-butoxycarbonyl)-2-bromoethylamine. Yield was 34.6%.

¹H NMR (270 MHz, DMSOd₆) δ10.40–10.30 (1H, m), 9.90–9.70 (3H, m), 8.00–7.80 (3H, m), 7.60–7.40 (3H, m), 7.40–7.30 (1H, m), 7.15–7.00 (2H, m), 4.70–4.50 (1H, m), 4.35–4.20 (2H, m), 3.50–2.40 (14H, m), 2.00–1.20 (16H, m).

MS(ESI positive) m/z: 502(M+H)³⁰.
IR(KBr): 3396, 1688 cm⁻¹
Anal. Calcd for $C_{31}H_{43}N_5O.3HCl.3H_2O$: C, 55.98; H, 7.88; N, 10.53. Found: C, 56.08; H, 7.93; N, 10.58.

Example 79
1-[1-(1-Phenylcycloheptyl)-4-piperidyl]-3-[3-(3pyridinyl)propyl]-1,3-dihydro-2H-1,3-benzimidazol-2-one This was prepared according to the procedure of Preparation 18 using 3-(3-methanesulfonyloxypropyl)pyridine (this was reported by K. Kawamura et al. JP 61015847) instead of N-(t-butoxycarbonyl)-2-bromoethylamine. Total yield was 8%.

¹H NMR (270 MHz, CDCl₃) δ8.47–8.41 (2H, m), 7.56–7.46 (3H, m), 7.40–6.87 (8H, m), 4.27–4.19 (1H, m), 3.91 (2H, t, J=7.1 Hz), 2.99–2.90 (2H, m), 2.70 (2H, dd, J=7.6, 8.2 Hz), 2.33–1.98 (8H, m),1.84–1.40 (12H, m).

MS(ESI positive) m/z: 509(M+H)⁺.
This free amine was converted to hydrochloride salt.
IR(KBr): 3400, 1684 cm⁻¹

Example 80
4-(2{2-Oxo-3-[1-(1-Phenylcycloheptyl)-4-piperidinyl]-2,3-dihydro-1H-benzimidazol-1-yl}ethyl)tetrahydro-1(2H)-pyrazinecarboximidamide trihydrochloride This was prepared according to the procedure of Example 65 using Example 78. Total yield was 23.5%.

¹H NMR (270 MHz, DMSOd₆) δ6 10.40–10.20 (1H, m), 8.00–7.60 (7H, m), 7.60–7.30 (5H, m), 7.15–7.00 (2H, m), 4.70–4.50 (1H, m), 4.35–4.20 (2H, m), 4.20–2.40 (14H, m), 1.90–1.40 (16H, m).

MS(ESI positive) m/z: 544(M+H)⁺.
IR(KBr): 3334, 1700 cm-1
Anal. Calcd for $C_{32}H_{45}N_7O.3HCl.5H_2O$: C, 51.72; H, 7.87; N, 13.19. Found: C, 52.11; H,7.85; N, 12.90.

Example 81
3-Butyl-1-[1-(1-Phenylcycloheptyl)-4-piperidinyl]-1,3-dihydro-2H- benzimidazol-2-one This was prepared according to the procedure of Preparation 18 using 4-bromobutane instead of N-(t-butoxycarbonyl)-2-bromoethylamine. Total yield was 47.5%.

¹H NMR (270 MHz, CDCl₃) δ7.55–7.46 (2H, m), 7.36–7.28 (2H, m), 7.25–7.17 (2H m), 7.10–6.95 (3H, m), 4.30–4.17 (1H, m), 3.85 (2H, t, J=7.2 Hz), 3.00–2.90 (2H, m), (2.35–2.00 (8H, m), 1.84–1.30 (14H, m), 0.94 (3H. t, J=7.4 Hz).

MS(ESI positive) m/z: 446(M+H)⁺.
This free amine was converted to hydrochloride salt.
IR(KBr): 3400, 1684 cm⁻¹
Anal. Calcd for $C_{29}H_{39}N_3O.HCl.0.8H_2O$: C. 70.15; H, 8.44; N, 8.46. Found: C, 70.18; H, 8.73; N, 8.48.

Example 82
1-Benzyl-3-[1-(1-Phenylcycloheptyl)-4-piperidinyl-]1,3-dihydro-2H-benzimidazol-2-one This was prepared according to the procedure of Preparation 18 using benzyl bromide instead of N-(t-butoxycarbonyl)-2-bromoethylamine. Total yield was 38.4%.

¹H NMR (270 MHz, CDCl₃) δ7.55–7.47 (2H, m), 7.36–7.16 (9H, m), 7.08–6.84 (3H, m), 5.04 (2H, s), 4.33–4.22 (1H, m), 3.00–2.90 (2H, m), 2.34–2.00 (8H, m), 1.84–1.40 (10H, m).

MS(ESI positive) m/z: 480(M+H)⁺.
This free amine was converted to hydrochloride salt.
IR(KBr): 3379, 1697 cm⁻¹
Anal. Calcd for $C_{32}H_{37}N_3O.HCl0.2H_2O$: C, 73.95; H, 7.45; N, 8.08. Found: C, 74.03; H, 7.60; N, 8.16.

Example 83
2-Amino-N-(2-{2-oxo-3-[1-(1-phenylcycloheptyl)-4-piperidinyl]-2,3-dihydro-1H-benzimidazol-1-yl}ethyl) acetamide dihydrochloride This was prepared according to the procedure of Example 68 using N-(t-butoxycarbonyl)glycine instead of N-(t-butoxycarbonyl)-L-proline. Total yield was 71.3%.

¹H NMR (270 MHz, DMSOd₆) δ10.40–10.25 (1H, m), 8.65–8.55 (1H, m), 8.25–8.05 (3H, m), 7.90–7.80 (3H, m), 7.60–7.40 (3H, m), 7.20–7.00 (3H, m), 4.70–4.50 (1H, m), 3.95–3.80 (2H, m), 3.50–2.40 (8H, m), 1.95–1.20 (16H, m).

MS m/z(EI direct): 489(M⁺), 412, 356, 315, 275, 235, 82.
IR(KBr): 3416, 1686 cm⁻¹
Anal. Calcd for $C_{29}H_{39}N_5O_2.2HCl.1.7H_2O$: C, 58.72; H, 7.54; N, 11.81. Found: C, 58.98; H, 7.93; N, 11.53.

Example 84
1-{2-[4-(2-Aminoacetyl)piperazino]ethyl}-3-[1-(1-phenylcycloheptyl)-4-piperidinyl]-1,3-dihydro-2H-benzimidazol-2-one trihydrochloride This was prepared according to the procedure of Example 83 using Example 78 instead of N-(t-butoxycarbonyl) glycine. Total yield was 83.6%.

¹H NMR (270 MHz, DMSOd₆) δ10.50–10.35 (1H, m), 8.40–8.20 (3H, m), 8.00–7.80 (3H, m), 7.60–7.35 (4H, mn), 7.15–7.00 (2H. m), 4.70–4.50 (1H, m), 4.50–4.25 (3H, m), 4.10–2.40 (16H, m), 1.95–1.20 (16H, m).

MS m/z(EI direct): 558(M⁺), 501, 386, 304, 172, 129, 91.
IR(KBr): 3392, 1674 cm⁻¹
Anal. Calcd for $C_{33}H_{46}N_6O_2.3HCl.2.7H_2O$: C, 55.30; H, 7.65; N, 11.72. Found: C, 55.51; H, 8.05; N, 11.73.

Example 85
N-(2-{2-Oxo-3-[1-(1-Phenylcycloheptyl)-4-piperidinyl]-2,3-dihydro-1H-benzimidazol-1-yl}ethyl) methanesulfonamide This was prepared according to the procedure of Example 67 using methanesulfonyl chloride instead of acetyl chloride. Total yield was 33.9%.

¹H NMR (270 MHz, CDCl₃) δ7.55–7.46 (2H, m), 7.36–7.28 (2H, m), 7.26–7.18 (2H, m), 7.14–7.04 (3H, m), 5.24–5.16 (1H, m), 4.26–4.10 (1H, m), 4.05 (2H, t, J=5.9Hz), 3.50 (2H, dt, J=5.9, 5.9 Hz), 3.00–2.90 (2H, m), 2.85 (3H, s), 2.32–2.19 (4H, m), 2.12–2.00 (4H, m), 1.84–1.40 (10H, m).

MS m/z(EI): 510(M⁺), 453, 337, 225, 214, 172, 129, 91.
This free amine was converted to hydrochloride salt.
IR(KBr): 3400, 1686 cm⁻¹
Anal. Calcd for $C_{28}H_{38}N_4O_3S.HCl.MeOH.H_2O$: C, 59.51; H, 7.31; N, 9.91. Found: C, 59.23; H, 7.38; N, 9.77.

Example 86
1-Acetyl-3-[1-(1-phenylcycloheptyl)-4-piperidinyl]-1,3-dihydro-2H-benzimidazol-2-one A mixture of 1-[1-(1-phenylcycloheptyl)-4-piperidyl]-1,3-dihydro-2H-1,3-benzimidazol-2-one (60 mg, 0.154 mmol, this was prepared as Example 17), pyridine (1 ml), acetic anhydride (44 μl, 0.462 mmol), and dimethylaminopyridine (6 mg, 0.0462 mmol) was stirred at room temperature for 1 h. After evaporation of the solvent, the residue was purified by preparative TLC (acetone/hexane:1/2) to give 48.2 mg (72.5%) of colorless oil.

$^1$H NMR (270 MHz, CDCl$_3$) δ8.22 (1H, br.d, J=7.9 Hz), 7.55–7.47 (2H, m), 7.36–7.29 (2H, m), 7.26–7.08 (4H, m), 4.23–4.13 (1H, m), 3.02–2.92 (2H, m), 2.74 (3H, s), 2.34–2.00 (8H, m), 1.84–1.40 (10H, m).

MS m/z(EI): 431 (M$^+$), 375, 346, 254, 198, 117, 82.

This free amine was converted to fumarate salt, mp 252° C.

IR(KBr): 1728, 1709 cm$^{-1}$

Anal. Calcd for C$_{27}$H$_{33}$N$_3$O$_2$.C$_4$H$_4$O$_4$.0.3H$_2$O: C, 67.32; H, 6.85; N, 7.60. Found: C. 67.02; H, 6.46; N, 7.37.

Example 87
1-[1-(1-Phenylcycloheptyl)-4-piperidinyl]-3-[2-(2-pyrimidinylamino)ethyl]-1,3-dihydro-2H-benzimidazol-2-one A mixture of 1-(2-aminoethyl)-3-[1-(1-phenylcycloheptyl)-4-piperidinyl]-1,3-dihydro-2H-benzimidazol-2-one dihydrochloride (37.81 mg, 0.0751 mmol, this was prepared according to the procedure of Preparation 18 and Example 64). 2-bromopyridine (14 mg, 0.0901 mol), K$_2$CO$_3$ (36 mg, 0.263 mmol), and DMF (1 ml) was stirred at 60° C. for 4 h. The mixture was diluted with CH$_2$Cl$_2$, washed with water, dried (Na$_2$SO$_4$), filtered, and concentrated. The residue was purified by preparative TLC (acetone/hexane:2/3) to give 3.3 mg (8.6%) of colorless oil.

$^1$H NMR (270 MHz, CDCl$_3$) δ8.27 (2H, d, J=4.6 Hz), 7.56–7.45 (2H, m), 7.45–7.00 (7H, m), 6.54 (1H, t, J=4.9 Hz), 5.58–5.50 (1H, m), 4.35–4.15 (1H, m), 4.12 (2H, t, J=6.3 Hz), 3.75 (2H, dt, J=5.9, 6.3 Hz), 3.00–2.90 (2H, m), 2.32–2.00 (8H, m), 2.00–1.40 (10H, m).

MS m/z(EI): 510(M$^+$), 453, 337. 256, 91.

This free amine was converted to hydrochloride salt to give amorphous solid.

IR(KBr): 1678, 1632 cm$^{-1}$

Example 88
1-[1-(1-Phenylcycloheptyl)-4-piperidinyl]-3-{2-[4-(2-pyrimidinyl)piperazino]ethyl}-1,3-dihydro-2H-benzimidazol-2-one This was prepared according to the procedure of Example 87 using Example 78 as starting material. Total yield was 32.2%.

$^1$H NMR (270 MHz, CDCl$_3$) δ8.29 (2H, d, J=4.6 Hz), 7.56–7.47 (2H, m), 7.36–7.16 (4H, m), 7.10–7.00 (3H, m), 6.47 (1H, t. J=4.8 Hz), 4.28–4.16 (1H, m), 4.03 (2H, t, J=7.1 Hz), 3.80 (4H, t, J=4.9 Hz), 3.00–2.90 (2H, m), 2.71 (2H, t, J=7.1 Hz), 2.60 (4H, t, J=4.9 Hz), 2.36–2.00 (8H, m), 1.86–1.40 (10H, m).

MS m/z(EI): 579(M$^+$), 522, 502, 406, 325, 177, 91.

This free amine was converted to hydrochloride salt to give amorphous solid.

IR(KBr): 3400, 1692, 1624 cm$^{-1}$

Anal. Calcd for C$_{35}$H$_{45}$N$_7$O.3HCl.2H$_2$O: C, 57.97; H, 7.23; N, 13.52. Found: C, 58.19; H, 7.12; N, 13.52.

Example 89
1-(2-Aminoethyl)-3-[1-(1-phenylcyclohept-4-enyl)-4-piperidinyl]-1,3-dihydro-2H-benzimidazol-2-one dihydrochloride This was prepared according to the procedure of Example 64 using Example 60 as starting material. Total yield was 66%.

$^1$H NMR (270 MHz, DMSOd$_6$) δ8.20–7.80 (4H, m), 7.80–7.70 (2H, m), 7.60–7.45 (4H, m), 7.35–7.25 (1H, m), 7.15–7.00 (2H, m), 5.73 (2H, br.s), 4.60–4.40 (1H, m), 4.15–4.00 (2H, m), 3.60–3.50 (4H, m). 3.15–2.80 (8H, m), 2.60–2.40 (2H, m), 2.00–1.75 (4H, m)

MS(ESI positive) m/z: 431(M+H)$^+$.

IR(KBr): 3429, 1686, 1616 cm$^{-1}$

Anal. Calcd for C$_{27}$H$_{34}$N$_4$O.2HCl.1.5H$_2$O: C, 61.67; H, 7.59; N, 10.29. Found: C, 61.66; H, 7.91; N, 10.53.

The chemical structures of the compounds of Formula (I) prepared in the Examples 1 to 89, wherein n is 1, are summarized in the following table.

TABLE (I)

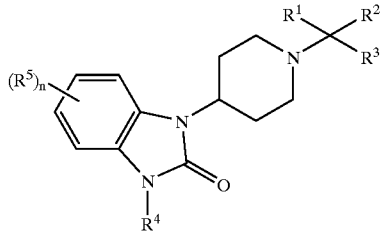

| Example No. | R$^1$ | R$^2$ | R$^3$ | R$^4$ | R$^5$ |
|---|---|---|---|---|---|
| 1 | cyclohexyl | | Ph | H | H |
| 2 | cyclohexyl | | benzyl | H | H |
| 3 | cyclohexyl | | methyl | H | H |
| 4 | cyclohexyl | | ethenyl | H | H |
| 5 | cyclohexyl | | 2-thienyl | H | H |
| 6 | cyclohexyl | | ethynyl | H | H |
| 7 | cyclohexyl | | propyl | H | H |
| 8 | cyclohexyl | | 4-Cl-Ph | H | H |
| 9 | cyclohexyl | | 4-methoxy-Ph | H | H |
| 10 | methyl | methyl | Ph | H | H |
| 11 | methyl | methyl | benzyl | H | H |
| 12 | methyl | methyl | 2-thienyl | H | H |
| 13 | methyl | methyl | 4-F-Ph | H | H |
| 14 | methyl | methyl | 4-methyl-Ph | H | H |
| 15 | methyl | methyl | 3-Ph-propyl | H | H |
| 16 | methyl | methyl | 4-methoxy-Ph | H | H |
| 17 | cycloheptyl | | Ph | H | H |

TABLE-continued

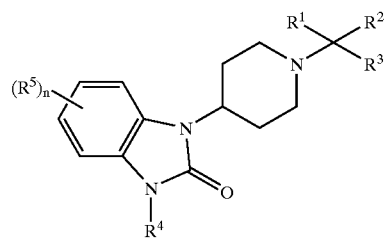

| Example No. | R$^1$ | R$^2$ | R$^3$ | R$^4$ | R$^5$ |
|---|---|---|---|---|---|
| 18 | cycloheptyl | | 2-thienyl | H | H |
| 19 | ethyl | ethyl | Ph | H | H |
| 20 | ethyl | ethyl | 2-thienyl | H | H |
| 21 | cyclobutyl | | Ph | H | H |
| 22 | cyclobutyl | | 2-thienyl | H | H |
| 23 | cyclopentyl | | Ph | H | H |
| 24 | cyclohexyl | | Ph | H | 6-Cl |
| 25 | cycloheptyl | | Ph | H | 6-Cl |
| 26 | cyclopropyl | | Ph | H | H |
| 27 | cycloheptyl | | Ph | methyl | H |
| 28 | cycloheptyl | | Ph | H | 5-methoxy |
| 29 | dimethylcyclohexyl | | Ph | H | H |
| 30 | cyclononyl | | n-propyl | H | H |
| 31 | bicyclo[4.3.0]nonan-8-yl | | Ph | H | H |
| 32 | cyclooctyl | | Ph | H | H |
| 33 | cyclononyl | | Ph | H | H |
| 34 | cyclodecyl | | Ph | H | H |
| 35 | cycloundecyl | | Ph | H | H |
| 36 | cyclododecyl | | Ph | H | H |
| 37 | cycloheptyl | | 4-F-Ph | H | H |
| 38 | cycloheptyl | | 3-F-Ph | H | H |
| 39 | cyclopheptyl | | 4-methoxy-Ph | H | H |
| 40 | cycloheptyl | | 3-methoxy-Ph | H | H |
| 41 | cycloheptyl | | 2-methoxy-Ph | H | H |
| 42 | 4-t-butylcyclohexyl | | Ph | H | H |
| 43 | cycloheptyl | | Ph | H | 4-F |
| 44 | cycloheptyl | | Ph | H | 5-F |
| 45 | cycloheptyl | | Ph | H | 6-F |
| 46 | cycloheptyl | | Ph | H | 5-Me |
| 47 | cycloheptyl | | Ph | H | 6-Me |
| 48 | cycloheptyl | | Ph | H | 5-CF$_3$ |
| 49 | cycloheptyl | | Ph | H | Ph-CO— |
| 50 | cycloheptyl | | Ph | H | 7-Cl |
| 51 | cycloheptyl | | Ph | H | 5,6-di-F |
| 52 | cycloheptyl | | Ph | H | 5,6-di-Cl |
| 53 | spiro[5.5]undecan-3-yl | | propyl | H | H |
| 54 | isopropylidenecyclohexyl | | propyl | H | H |
| 55 | cyclononyl | | methyl | H | H |
| 56 | cyclononyl | | ethyl | H | H |
| 57 | cyclooctyl | | methyl | H | H |
| 58 | cyclooctyl | | ethyl | H | H |
| 59 | cyclooctyl | | propyl | H | H |
| 60 | cyclohept-4-enyl | | Ph | H | H |
| 61 | cyclohept-4-enyl | | methyl | H | H |
| 62 | cyclohept-4-enyl | | ethyl | H | H |
| 63 | cyclohept-4-enyl | | propyl | H | H |
| 64 | cycloheptyl | | Ph | aminoethyl | H |
| 65 | cycloheptyl | | Ph | guanidinoethyl | H |
| 66 | cycloheptyl | | Ph | methylaminoethyl | H |
| 67 | cycloheptyl | | Ph | acetylaminoethyl | H |
| 68 | cycloheptyl | | Ph | L-prolinamidoethyl | H |
| 69 | cycloheptyl | | Ph | pyridyl-CONH-ethyl | H |
| 70 | cycloheptyl | | Ph | aminopropyl | H |
| 71 | cycloheptyl | | Ph | aminohexyl | H |
| 72 | cycloheptyl | | Ph | piperidinoethyl | H |
| 73 | cycloheptyl | | Ph | morpholinoethyl | H |
| 74 | cycloheptyl | | Ph | dimethylaminoethyl | H |
| 75 | cycloheptyl | | Ph | diisopropylaminoethyl | H |
| 76 | cycloheptyl | | Ph | piperidinylethyl | H |
| 77 | cycloheptyl | | Ph | pyrrolylethyl | H |
| 78 | cycloheptyl | | Ph | piperazinoethyl | H |
| 79 | cycloheptyl | | Ph | pyridinylpropyl | H |

TABLE-continued

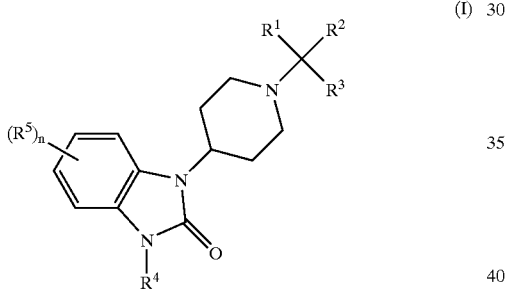

(I)

| Example No. | $R^1$ | $R^2$ | $R^3$ | $R^4$ | $R^5$ |
|---|---|---|---|---|---|
| 80 | cycloheptyl | Ph | | amidinopiperazinoethyl | H |
| 81 | cycloheptyl | Ph | | n-butyl | H |
| 82 | cycloheptyl | Ph | | benzyl | H |
| 83 | cycloheptyl | Ph | | $NH_2\text{—}CH_2CONH\text{—}(CH_2)_2\text{—}$ | H |
| 84 | cycloheptyl | Ph | | aminoacetylpiperazinoethyl | H |
| 85 | cycloheptyl | Ph | | methylsulfonylaminoethyl | H |
| 86 | cycloheptyl | Ph | | acetyl | H |
| 87 | cycloheptyl | Ph | | pyrimidinylaminoethyl | H |
| 88 | cycloheptyl | Ph | | pyrimidinylpiperazinoethyl | H |
| 89 | cyclohept-4-enyl | Ph | | aminoethyl | H |

What is claimed is:

1. A compound of the following formula:

(I)

or the pharmaceutically acceptable salts thereof, wherein
$R^1$ and $R^2$ are independently $C_1$–$C_4$ alkyl; or
$R^1$ and $R^2$, taken together with the carbon atom to which they are attached, form a mono-, bi-, tri- or spiro-cyclig group having 6 to 13 carbon atoms, wherein the cyclic group is optionally substituted by one to five substituents independently selected from $C_1$–$C_4$ alkyl, $C_2$–$C_4$ alkylene, $C_1$–$C_4$ alkoxy, hydroxy, oxo, $=CH_2$ and $=CH\text{—}C_1$–$C_4$ alkyl;
$R^3$ is $C_1$–$C_7$ alkyl, $C_2$–$C_5$ alkenyl, $C_2$–$C_5$ alkynyl, phenyl-$C_1$–$C_5$ alkyl, phenyl optionally substituted by one to three substituents independently selected from fluorine, $C_1$–$C_3$ alkyl and $C_1$–$C_3$ alkoxy, or a heteroaryl group selected from furyl, thienyl, pyrrolyl and pyridyl, wherein said heteroaryl group is optionally substituted by one to three substituents independently selected from halo, $C_1$–$C_3$ alkyl and $C_1$–$C_3$ alkoxy, with the proviso that when both $R^1$ and $R^2$ are $C_1$–$C_4$ alkyl, then $R^3$ is other than $C_1$–$C_7$ alkyl, $C_2$–$C_5$ alkenyl and $C_2$–$C_5$ alkynyl;
$R^4$ is selected from:
1) hydrogen,
2) optionally mono- or di- substituted, $C_1$–$C_8$ alkyl $C_3$–$C_7$ cycloalkyl, $C_2$–$C_8$ alkenyl, $C_2$–$C_8$ alkynyl, $C_1$–$C_6$ alkyl-Z—, $C_1$–$C_6$ alkyl-Z—($C_1$–$C_6$)alkyl, $C_3$–$C_7$ cycloalkyl-Z—($C_1$–$C_6$)alkyl, $C_2$–$C_6$ alkenyl-Z—($C_1$–$C_6$)alkyl or $C_2$–$C_6$ alkynyl-Z—($C_1$–$C_6$) alkyl, wherein Z is selected from O, S, SO, $SO_2$, CO, $CO_2$, OCO, NR, CONR and NRCO wherein R is hydrogen or $C_1$–$C_6$ alkyl, and the substituents to be attached to the alkyl, alkenyl, alkynyl or cycloalkyl moiety are independently selected from halo, hydroxy, carboxy, amino, mono- or di-($C_1$–$C_4$ alkyl) amino, hydrazino, azido, ureido, amidino and guanidino; or
3) optionally mono- or di- substituted, aryl, heterocyclic, aryl($C_1$–$C_5$)alkyl, heterocyclic($C_1$–$C_5$) alkyl, heterocyclic-heterocyclic($C_1$–$C_5$)alkyl, aryl-heterocyclic($C_1$–$C_5$)alkyl, heterocyclic-Z—($C_1$–$C_5$) alkyl, aryl-Z—($C_1$–$C_5$)alkyl, aryl($C_1$–$C_5$)alkyl-Z—($C_1$–$C_5$)alkyl, or heterocyclic($C_1$–$C_5$)alkyl-Z—($C_1$–$C_5$)alkyl, wherein Z is selected from O, S, SO, $SO_2$, CO, $CO_2$, OCO, NR, CONR and NRCO, wherein R is hydrogen or $C_1$–$C_6$ alkyl, and the substituents to be attached to the aryl or heterocyclic moiety are independently selected from halo, hydroxy, carboxy, $C_1$–$C_4$ alkyl, halo $C_1$–$C_4$ alkyl, $C_1$–$C_4$ alkoxy, $C_1$–$C_4$ alkyl-CO—, amino($C_1$–$C_4$) alkyl-CO—, phenyl, benzyl, amino, mono- or di-($C_1$–$C_4$ alkyl)amino, hydrazino, azido, ureido, amidino and guanidino;
$R^5$ is independently selected from halo, $C_1$–$C_3$ alkyl, $C_1$–$C_3$ alkoxy, $C_1$–$C_3$ alkylsulfonyl, $CF_3$, carboxy, hydroxy, amino, alkylamino, acylamino, arylcarbonyl, alkylcarbonyl and hydroxyalkyl; and
n is 0, 1, 2, 3 or 4.

2. A compound according to claim 1, wherein
$R^1$ and $R^2$ are independently $C_1$–$C_4$ alkyl; or
$R^1$ and $R^2$, taken together with the carbon atom to which they are attached, form a monocyclic group selected from cyclo-$C_3$–$C_{14}$ alkyl and cyclo-$C_4$–$C_{14}$ alkenyl, a bicyclic group selected from decahydronaphthalene, bicyclo[2.2.1.]heptane, bicyclo[4.3.0.]nonane, bicyclo[3.2.1]octane and bicyclo[3.2.0]heptene, bicyclo[3.3.1]nonane, a tricyclic group selected from adamantane and tricyclo[5.2.1.0$^{2,6}$]decane, or a spirocyclic group selected from spiro[5.5]undecanyl and spiro[4.5]decanyl, wherein the cyclic group is optionally substituted by one to three substituents independently selected from $C_1$–$C_4$ alkyl, $C_2$–$C_4$ alkylene, $C_1$–$C_4$ alkoxy, hydroxy and oxo;

$R^3$ is $C_1$–$C_7$ alkyl, $C_2$–$C_5$ alkenyl, $C_2$–$C_5$ alkynyl, phenyl-$C_1$–$C_3$ alkyl, phenyl optionally substituted by one to three substituents independently selected from fluorine, $C_1$–$C_3$ alkyl and $C_1$–$C_3$ alkoxy, or thienyl;

$R^4$ is selected from:
1) hydrogen;
2) optionally mono- or di- substituted, $C_1$–$C_8$ alkyl, $C_3$–$C_7$ cycloalkyl, $C_2$–$C_6$ alkenyl, $C_1$–$C_6$ alkyl-Z—($C_1$–$C_6$)alkyl, $C_3$–$C_7$ cycloalkyl-Z—($C_1$–$C_6$)alkyl or $C_2$–$C_6$ alkenyl-Z—($C_1$–$C_6$)alkyl, wherein Z is selected from NH, O, S, SO, $SO_2$, CO, $CO_2$, OCO, CONH and NHCO, and the substituents are independently selected from halo, hydroxy, amino, mono- or di-($C_1$–$C_4$ alkyl)amino, hydrazino, azido, ureido, amidino and guanidino; or
3) optionally mono- or di- substituted, aryl, heterocyclic, aryl($C_1$–$C_5$)alkyl, heterocyclic($C_1$–$C_5$)alkyl, heterocyclic-piperazino($C_1$–$C_5$)alkyl, heterocyclic-amino($C_1$–$C_5$)alkyl, aryl-Z—($C_1$–$C_5$)alkyl, heterocyclic-Z—($C_1$–$C_5$)alkyl, aryl($C_1$–$C_5$)alkyl-Z—($C_1$–$C_5$)alkyl or heterocyclic($C_1$–$C_5$)alkyl-Z—($C_1$–$C_5$)alkyl, wherein the aryl group is selected from phenyl and naphthyl, and the heterocyclic group is selected from furyl, thiophenyl, pyridyl, pyrimidiny, pyrazinyl, pyridazinyl, aziridinyl, azethidinyl, pyrrolidinyl, piperidino, hexamethyleneimino, piperazino and morpholino;

Z is selected from NH, O, S, SO, $SO_2$, CO, $CO_2$, OCO, CONH and NHCO; and the substituents are independently selected from halo, hydroxy, carboxy, $C_1$–$C_4$ alkyl, halo $C_1$–$C_4$ alkyl, $C_1$–$C_4$ alkoxy, $C_1$–$C_4$ alkyl-CO—, phenyl, benzyl, amino, mono- or di-($C_1$–$C_4$ alkyl)amino, hydrazino, azido, ureido, amidino and guanidino; and $R^5$ is halo, $CF_3$ or $C_1$–$C_3$ alkoxy; and n is 0, 1, 2 or 3.

3. A compound according to claim 1, wherein $R^1$ and $R^2$ are independently $C_1$–$C_3$ alkyl, or taken together with the carbon atom to which they are attached, form a cyclic group selected from cyclopropyl, cyclobutyl, cyclopentyl, cyclohexyl, cycloheptyl, cyclooctyl, cyclononyl, cyclodecyl, cycloundecyl, cycloheptenyl, dimethylcyclohexyl, butylcyclohexyl, isopropylidenecyclohexyl, bicyclo[4.3.0]nonanyl and spiro[5.5]undecanyl; $R^3$ is $C_1$–$C_3$ alkyl, $C_2$–$C_3$ alkenyl, phenyl optionally substituted by chloro, fluoro or $C_1$–$C_3$ alkoxy, phenyl($C_1$–$C_3$)alkyl, ethenyl or thienyl; $R^4$ is hydrogen, ($C_1$–$C_6$)alkyl, ($C_1$–$C_6$)alkyl substituted by amino, guanidino, ($C_1$–$C_3$)alkylamino, acetylamino, pyrroryl-CO—NH—, pyridyl-CO—NH—, heterocyclic selected from piperidino, hexamethyleneimino, morpholino, pyrrolidino, pyrrolyl, pyridinyl, pyrimidinyl and pyrimidinylpiperazino; R5 is fluoro, chloro, ($C_1$–$C_3$)alkyl or ($C_1$–$C_3$) alkoxy; and n is 0, 1 or 2.

4. A compound according to claim 1, selected from
1-{1-[1-Methyl-1-(2-thienyl)ethyl]-4-piperidinyl}-1,3-dihydro-2H-1,3-benzimidazol-2-one,
1-[1-(1-Phenylcycloheptyl)-4-piperidinyl]-1,3-dihydro-2H-1,3-benzimidazol-2-one,
1-[4-Piperidinyl-1-(1-Propylcyclononyl)]-1,3-dihydro-2H-1,3-benzimidazol-2-one,
1-[1-(1-Phenylcyclooctyl)-4-piperidinyl]-1,3-dihydro-2H-1,3-benzimidazol-2-one,
1-[1-(1-Phenylcyclononyl)-4-piperidinyl]-1,3-dihydro-2H-1,3-benzimidazol-2-one,
1-{1-[1-(4-Fluorophenyl)cycloheptyl]-4-piperidinyl}-1,3-dihydro-2H-1,3-benzimidazol-2-one,
1-[1-(1-Methylcyclononyl)-4-piperidinyl]-1,3-dihydro-2H-1,3-benzimidazol-2-one,
1-[1-(1-Ethylcyclononyl)-4-piperidinyl]-1,3-dihydro-2H-1,3-benzimidazol-2-one,
1-[1-(1-Methylcyclooctyl)-4-piperidinyl]-1,3-dihydro-2H-1,3-benzimidazol-2-one,
1-[1-(1-Phenylcyclohept-4-enyl)-4-Piperidinyl]-1,3-dihydro-2H-1,3-benzimidazol-2-one,
1-(2-Aminoethyl)-3-[1-(1-phenylcycloheptyl)-4-piperidinyl]-1,3-dihydro-2H-benzimidazol-2-one,
1-(6-Aminohexyl)-3-[1-(1-phenylcycloheptyl)-4-piperidinyl]-1,3-dihydro-2H-benzimidazol-2-one,
1-(2-Aminoethyl)-3-[1-(1-phenylcyclohept-4-enyl)-4-piperidinyl]-1,3-dihydro-2H-benzimidazol-2-one, 1-[1-(1-phenylcycloheptyl)-4-piperidinyl]-3-(2-piperidinoethyl)-1,3-dihydro-2H-benzimidazol-2-one, and a salt thereof.

5. A compound according to claim 1 selected from 1-[1-(phenylcycloheptyl)-4-piperidinyl]-1,3-dihydro-2H-1,3-benzimidazol-2-one, 1-[1-(1-methylcyclononyl)-4-piperidinyl]-1,3-dihydro-2H-1,3-benzimidazol-2-one, 1-[1-(1-methylcyclooctyl)-4-piperidinyl]-1,3-dihydro-2H1,3-benzimidazol-2-one, 1-(6-aminohexyl)-3-[1-(1-phenylcycloheptyl)-4-piperidinyl]-1,3-dihydro-2H-benzimidazol-2-one, 1-[1-(1-phenylcycloheptyl)-4-piperidinyl]-3-(2-piperidinoethyl)-1,3-dihydro-2H-benzimidazol-2-one, and a salt thereof.

6. A pharmaceutical composition for the treatment of a disorder or condition mediated by ORL1-receptor and its endogenous ligands in a mammal, comprising an effective amount of the compound of claim 1, or a pharmaceutically acceptable salt thereof and a pharmaceutically acceptable carrier.

7. A method for treating a disorder or condition, the treatment of which can be effected or facilitated by binding to ORL1-receptor in a mammal comprising administering to a mammal in need of such treatment an effective amount of a compound of claim 1, or a pharmaceutically acceptable salt thereof.

* * * * *